(12) United States Patent
Mehrling (10) Patent No.: US 11,786,509 B2
(45) Date of Patent: *Oct. 17, 2023

(54) COMPOUNDS FOR TREATING TNBC

(71) Applicant: Purdue Pharma L.P., Stamford, CT (US)

(72) Inventor: Thomas Jorg Mehrling, Basel (CH)

(73) Assignee: Purdue Pharma L.P., Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/885,696

(22) Filed: Aug. 11, 2022

(65) Prior Publication Data

US 2023/0080216 A1     Mar. 16, 2023

Related U.S. Application Data

(63) Continuation of application No. 16/621,896, filed as application No. PCT/EP2018/065662 on Jun. 13, 2018, now Pat. No. 11,413,276.

(30) Foreign Application Priority Data

Jun. 13, 2017   (GB) .................................... 1709406

(51) Int. Cl.
   *A61K 31/4184*   (2006.01)
   *A61P 35/00*     (2006.01)
   *A61K 9/00*      (2006.01)
   *A61K 31/502*    (2006.01)
   *A61K 45/06*     (2006.01)

(52) U.S. Cl.
   CPC .......... *A61K 31/4184* (2013.01); *A61P 35/00* (2018.01); *A61K 9/0019* (2013.01); *A61K 31/502* (2013.01); *A61K 45/06* (2013.01)

(58) Field of Classification Search
   CPC .............. A61K 31/4184; A61K 9/0019; A61K 31/502; A61K 45/06; A61P 35/00
   USPC ........................................................ 514/394
   See application file for complete search history.

(56) References Cited

U.S. PATENT DOCUMENTS

| | | |
|---|---|---|
| 4,522,811 A | 6/1985 | Eppstein et al. |
| 5,134,127 A | 7/1992 | Stella et al. |
| 5,376,645 A | 12/1994 | Stella et al. |
| 5,571,534 A | 11/1996 | Jalonen et al. |

(Continued)

FOREIGN PATENT DOCUMENTS

| | | |
|---|---|---|
| CL | 0501-2003 | 3/2003 |
| CL | 2272-2005 | 9/2005 |

(Continued)

OTHER PUBLICATIONS

Advanced Accelerator Applications, Ongoing Clinical Studies with Advanced Accelerator Applications Pipeline Candidates. Retrieved online at: http://www.adacap.com/research-development/clinical-trials/. 6 pages, (2014).

(Continued)

*Primary Examiner* — Taylor V Oh
(74) *Attorney, Agent, or Firm* — McCarter & English, LLP; Yu Lu (57) ABSTRACT

There is provided tinostamustine or a pharmaceutically acceptable salt thereof for use in the treatment of triple negative breast cancer (TNBC) to a patient in need thereof.

14 Claims, 1 Drawing Sheet

(56) References Cited

U.S. PATENT DOCUMENTS

| | | |
|---|---|---|
| 5,874,418 A | 2/1999 | Stella et al. |
| 6,046,177 A | 4/2000 | Stella et al. |
| 6,087,367 A | 7/2000 | Breslow et al. |
| 6,133,248 A | 10/2000 | Stella |
| 6,214,852 B1 | 4/2001 | Kim et al. |
| 6,407,079 B1 | 6/2002 | Muller et al. |
| 8,461,350 B2 | 6/2013 | Brittain et al. |
| 8,609,864 B2 | 12/2013 | Chen et al. |
| 8,962,855 B2 | 2/2015 | Chen et al. |
| 9,096,627 B2 | 8/2015 | Chen et al. |
| 9,376,395 B2 | 6/2016 | Chen et al. |
| RE46,144 E | 9/2016 | Chen et al. |
| 9,889,147 B2 | 2/2018 | Utku |
| 9,993,482 B2 | 6/2018 | Mehrling |
| 10,118,901 B2 | 11/2018 | Chen et al. |
| 10,406,138 B2 | 9/2019 | Mehrling et al. |
| 10,744,120 B2 | 8/2020 | Mehrling et al. |
| 11,266,631 B2 | 3/2022 | Mehrling et al. |
| 11,318,117 B2 | 5/2022 | Mehrling et al. |
| 11,413,276 B2 * | 8/2022 | Mehrling ........... A61K 31/4164 |
| 11,419,853 B2 | 8/2022 | Mehrling et al. |
| 2002/0076409 A1 | 6/2002 | March et al. |
| 2006/0079528 A1 | 4/2006 | Finn et al. |
| 2006/0159713 A1 | 7/2006 | Brittain et al. |
| 2008/0146556 A1 | 6/2008 | Diebold et al. |
| 2010/0022512 A1 | 1/2010 | Wisdom et al. |
| 2010/0216858 A1 | 8/2010 | Popek et al. |
| 2011/0190363 A1 | 8/2011 | Drager et al. |
| 2011/0269706 A1 | 11/2011 | Chen et al. |
| 2011/0311624 A1 | 12/2011 | Loury et al. |
| 2012/0289570 A1 | 11/2012 | Lengyel et al. |
| 2013/0030237 A1 | 1/2013 | Theuer |
| 2013/0209558 A1 | 8/2013 | Patzak et al. |
| 2014/0303218 A1 | 10/2014 | Chen et al. |
| 2015/0086551 A1 | 3/2015 | Chen et al. |
| 2015/0231198 A1 | 8/2015 | Carniti et al. |
| 2017/0095482 A1 | 4/2017 | Mehrling |
| 2017/0151218 A1 | 6/2017 | Mehrling et al. |
| 2018/0098969 A1 | 4/2018 | Mehrling et al. |
| 2019/0343807 A1 | 11/2019 | Mehrling et al. |
| 2020/0113870 A1 | 4/2020 | Mehrling |
| 2020/0261423 A1 | 8/2020 | Mehrling |
| 2021/0059989 A1 | 3/2021 | Mehrling et al. |
| 2021/0346351 A1 | 11/2021 | Mehrling et al. |
| 2022/0016084 A1 | 1/2022 | Hilgier et al. |
| 2022/0016085 A1 | 1/2022 | Hilgier et al. |
| 2022/0280485 A1 | 9/2022 | Mehrling et al. |
| 2022/0401417 A1 | 12/2022 | Mehrling et al. |
| 2023/0049350 A1 | 2/2023 | Mehrling et al. |

FOREIGN PATENT DOCUMENTS

| | | |
|---|---|---|
| CL | 3232-2006 | 11/2006 |
| CN | 1764648 A | 4/2006 |
| CN | 101084876 A | 12/2007 |
| CN | 101928234 A | 12/2010 |
| CN | 102993102 A | 3/2013 |
| DE | 34727 A1 | 12/1964 |
| EP | 0717638 B1 | 3/2002 |
| EP | 3148529 A1 | 4/2017 |
| JP | 2007-531793 A | 11/2007 |
| KR | 10-2001-0031896 A | 4/2001 |
| WO | WO-1995/030442 A1 | 11/1995 |
| WO | WO-2002/010161 A1 | 2/2002 |
| WO | WO-2002/22577 A2 | 3/2002 |
| WO | WO-2002/026696 A1 | 4/2002 |
| WO | WO-2002/055017 A2 | 7/2002 |
| WO | WO-2004/076386 A2 | 9/2004 |
| WO | WO-2005/013958 A1 | 2/2005 |
| WO | WO-2005/097747 A1 | 10/2005 |
| WO | WO-2006/120456 A1 | 11/2006 |
| WO | WO-2007/134169 A2 | 11/2007 |
| WO | WO-2008/050125 A1 | 5/2008 |
| WO | WO-2008/067027 A2 | 6/2008 |
| WO | WO-2009/036016 A1 | 3/2009 |
| WO | WO-2009/067453 A1 | 5/2009 |
| WO | WO-2009/100045 A1 | 8/2009 |
| WO | WO-2010/042568 A1 | 4/2010 |
| WO | WO-2010/075542 A1 | 7/2010 |
| WO | WO-2010/085377 A2 | 7/2010 |
| WO | WO-2010/097700 A1 | 9/2010 |
| WO | WO-2011/017448 A1 | 2/2011 |
| WO | WO-2013/039488 A1 | 3/2013 |
| WO | WO-2013/040286 A2 | 3/2013 |
| WO | WO-2013/113838 A1 | 8/2013 |
| WO | WO-2015/085289 A1 | 6/2015 |
| WO | WO-2015/180865 A1 | 12/2015 |
| WO | WO-2015/181154 A1 | 12/2015 |
| WO | WO-2015/181156 A1 | 12/2015 |
| WO | WO-2015/181157 A1 | 12/2015 |
| WO | WO-2016/087950 A1 | 6/2016 |
| WO | WO-2017/067474 A1 | 4/2017 |
| WO | 2018/229133 A1 | 12/2018 |

OTHER PUBLICATIONS

Aguado Bueno et al., Preliminary Experience of the Spanish Compassionate Use Registry of Bendamustine in Patients with Relapsed and/or Refractory Multiple Myeloma. Blood. 2012;120(21), Abstract 4035.

Al-Ani et al., Changes in urinary metabolomic profile during relapsing renal vasculitis. Sci Rep. Dec. 1, 2016;6:38074. 11 pages.

Alfarouk et al., Resistance to cancer chemotherapy: failure in drug response from ADME to P-gp. Cancer Cell Int. Jul. 15, 2015;15:71.

American Cancer Society, How does chemotherapy affect the risk of second cancers? Retrieved online at: https://www.cancer.org/treatment/treatments-and-side-effects/physical-side-effects/second-cancers-in-adults/chemotherapy.html. 5 pages (2017).

Anastasia et al., Bendamustine for Hodgkin lymphoma patients failing autologous or autologous and allogeneic stem cell transplantation: a retrospective study of the Fondazione Italiana Linfomi. Br J Haematol. Jul. 2014;166(1):140-2.

Andersson et al., Discovery of novel drug sensitivities in T-PLL by high-throughput ex vivo drug testing and mutation profiling. Leukemia. Aug. 14, 2017. pp. 1-14.

Andersson et al., Primary T-Prolymphocytic Leukemia (T-PLL) Cells Are Sensitive To BCL-2 and HDAC Inhibitors: Results From High-Throughput Ex Vivo Drug Testing. Blood. 2013;122:3828. 6 pages.

Angelucci et al., Suberoylanilide hydroxamic acid partly reverses resistance to paclitaxel in human ovarian cancer cell lines. Gynecol Oncol. Dec. 2010;119(3):557-63.

Arun et al., The PARP inhibitor AZD2281 (Olaparib) induces autophagy/mitophagy in BRCA1 and BRCA2 mutant breast cancer cells. Int J Oncol. Jul. 2015;47(1):262-8.

Attal et al., Lenalidomide, Bortezomib, and Dexamethasone with Transplantation for Myeloma. The New England Journal of Medicine. Apr. 6, 2017;376:1311-1320.

Audeh et al., Oral poly(ADP-ribose) polymerase inhibitor olaparib in patients with BRCA1 or BRCA2 mutations and recurrent ovarian cancer: a proof-of-concept trial. Lancet. Jul. 24, 2010;376(9737):245-51.

Bachmann et al., Epigenetic silencing of BIM in glucocorticoid poor-responsive pediatric acute lymphoblastic leukemia, and its reversal by histone deacetylase inhibition. Blood. Oct. 21, 2010;116(16):3013-22. .

Bagchi, Bendamustine for advanced sarcoma. Lancet Oncol. Aug. 2007;8(8):674.

Baker et al., Investigation of bendamustine HCL in a phase 2 study in women with resistant ovarian cancer. Invest New Drugs. Feb. 2013;31(1):160-6.

Balfour et al., Bendamustine. Drugs. 2001;61(5):631-8.

Barendsen et al., Inhibition of TPA-induced monocytic differentiation in THP-1 human monocytic leukemic cells by staurosporine, a potent protein kinase C inhibitor. Leuk Res. 1990;14(5):467-74.

Bender, Across the divide. The blood-brain barrier represents a formidable obstacle for cancer drugs. Nature. Sep. 27, 2018;561:S46-S47.

(56) References Cited

OTHER PUBLICATIONS

Berenson et al., Phase I/II trial assessing bendamustine plus bortezomib combination therapy for the treatment of patients with relapsed or refractory multiple myeloma. Br J Haematol. Feb. 2013;160(3):321-30.
Bernhard et al., Quality of life and quality-adjusted survival (Q-TWiST) in patients receiving dose-intensive or standard dose chemotherapy for high-risk primary breast cancer. Br J Cancer. Jan. 15, 2008;98(1):25-33.
Besse et al., The first in class, alkylator-histone-deacetylase-inhibitor fusion molecule EDO-S101 in combination with proteasome inhibitors induces highly synergistic pro-apoptotic signaling through UPR activation and suppression of c-Myc and BCL2 in multiple meyloma. ASH, 2016.
Besse et al., The first-in-class alkylating HDAC inhibitor EDO-S101 is highly synergistic with proteasome inhibition against multiple myeloma through activation of multiple pathways. Blood Cancer J. Jul. 2017;7(7):e589. 4 pages.
Besse et al., The First-in-Class, Alkylator-Histone-Deacetylase-Inhibitor Fusion Molecule EDO-S101 in Combination with Proteasome Inhibitors Induces Highly Synergistic Pro-Apoptotic Signaling through UPR Activation and Suppression of c-MYC and BCL2 in Multiple Myeloma. 58th ASH Annual Meeting, San Diego, Dec. 3-6, 2016, Publication No. 4466. 1 page.
Biete et al., Whole abdominal radiotherapy in ovarian cancer. Rep Pract Oncol Radiother. Mar. 23, 2010;15(2):27-30.
Bijnsdorp et al., Analysis of Drug Interactions. Cancer Cell Culture, Methods and Protocols, Second Edition, Methods in Molecular Biology, vol. 731. Ian A. Cree (Ed.), Humana Press. Chapter 34, pp. 421-434, (2011).
Blattmann et al., Enhancement of radiation response in osteosarcoma and rhabdomyosarcoma cell lines by histone deacetylase inhibition. Int J Radiat Oncol Biol Phys. Sep. 1, 2010;78(1):237-45.
Bose et al., Histone deacetylase inhibitor (HDACI) mechanisms of action: emerging insights. Pharmacol Ther. Sep. 2014;143(3):323-36.
Botrugno et al., Molecular pathways: old drugs define new pathways: non-histone acetylation at the crossroads of the DNA damage response and autophagy. Clin Cancer Res. May 1, 2012;18(9):2436-42.
Braga et al., Crystal Polymorphism and Multiple Crystal Forms. Struct Bond. 2009;132:25-50.
Brewster et al., Cyclodextrins as pharmaceutical solubilizers. Adv Drug Deliv Rev. Jul. 30, 2007;59(7):645-66.
Bruce et al., Glioblastoma Multiforme Treatment & Management. Medscape. Retrieved online at: https://emedicine.medscape.com/article/283252-treatment. 20 pages. Jun. 14, 2017.
Buglio et al., Histone deacetylase inhibitors in Hodgkin lymphoma. Invest New Drugs. Dec. 2010;28 Suppl 1:S21-7.
Buglio et al., Vorinostat inhibits STAT6-mediated TH2 cytokine and TARC production and induces cell death in Hodgkin lymphoma cell lines. Blood. Aug. 15, 2008;112(4):1424-33.
Cai et al., Combination of bendamustine and entinostat synergistically inhibits proliferation of multiple myeloma cells via induction of apoptosis and DNA damage response. Cancer Lett. Jul. 28, 2013;335(2):343-50.
Cai et al., Discovery of 7-(4-(3-ethynylphenylamino)-7-methoxyquinazolin-6-yloxy)-N-hydroxyheptanamide (CUDc-101) as a potent multi-acting HDAC, EGFR, and HER2 inhibitor for the treatment of cancer. J Med Chem. Mar. 11, 2010;53(5):2000-9.
Cai et al., Solubilization of vorinostat by cyclodextrins. J Clin Pharm Ther. Oct. 2010;35(5):521-6.
Campos et al., Expression of nuclear receptor corepressors and class I histone deacetylases in astrocytic gliomas. Cancer Sci. Feb. 2011;102(2):387-92.
Chamberlain et al., Salvage therapy with bendamustine for methotrexate refractory recurrent primary CNS lymphoma: a retrospective case series. J Neurooncol. May 2014;118(1):155-62.
Chamberlain et al., Salvage therapy with single agent bendamustine for recurrent glioblastoma. J Neurooncol. Dec. 2011;105(3):523-30.
Chavez et al., Triple negative breast cancer cell lines: one tool in the search for better treatment of triple negative breast cancer. Breast Dis. 2010;32(1-2):35-48.
Chen et al., A 71-gene signature of TRAIL sensitivity in cancer cells. Mol Cancer Ther. Jan. 2012;11(1):34-44.
Chen et al., Dexamethasone and vorinostat cooperatively promote differentiation and apoptosis in Kasumi-1 leukemia cells through ubiquitination and degradation of AML1-ETO. Zhonghua Xue Ye Xue Za Zhi. Sep. 2013;34(9):741-4.
Chen et al., Discovery of a Novel, Efficient, and Scalable Route to Bendamustine Hydrochloride: The API in Treanda. Org Process Res Dev. 2011;15(5):1063-1072.
Chesi et al., Drug response in a genetically engineered mouse model of multiple myeloma is predictive of clinical efficacy. Blood. Jul. 12, 2012;120(2):376-85.
Chesi et al., Identification of Novel Therapeutic Targets in the Clinically Predictive Vk*MYC Mouse Model of Multple Myeloma. ASH, 2 pages. 2014.
Chesi et al., Identification of Novel Therapeutic Targets in the Clinically Predictive Vk*MYC Mouse Model of Multple Myeloma. Blood. 2014;124:415.
Chisholm et al., Emergence of drug tolerance in cancer cell populations: an evolutionary outcome of selection, nongenetic instability, and stress-induced adaptation. Cancer Res. Mar. 15, 2015;75(6):930-9.
Chiu et al., Suberoylanilide hydroxamic acid, an inhibitor of histone deacetylase, enhances radiosensitivity and suppresses lung metastasis in breast cancer in vitro and in vivo. PLoS One. Oct. 10, 2013;8(10):e76340. 12 pages.
Choi et al., Enhanced cytotoxic effect of radiation and temozolomide in malignant glioma cells: targeting PI3K-AKT-mTOR signaling, HSP90 and histone deacetylases. BMC Cancer. Jan. 13, 2014;14:17. 12 pages.
Chou, Drug combination studies and their synergy quantification using the Chou-Talalay method. Cancer Res. Jan. 15, 2010;70(2):440-6.
Chow et al., In vitro induction of apoptosis of neoplastic cells in low-grade non-Hodgkin's lymphomas using combinations of established cytotoxic drugs with bendamustine. Haematologica. May 2001;86(5):485-93.
Ciavatta et al., Epigenetic basis for aberrant upregulation of autoantigen genes in humans with ANCA vasculitis. J Clin Invest. Sep. 2010;120(9):3209-19.
Ciusani et al., Valproic acid increases the in vitro effects of nitrosureas on human glioma cell lines. Oncol Res. 2007;16(10):453-63.
ClinicalTrials.gov, A Phase 1 Study to Investigate the Safety, Pharmacokinetic Profiles and the Efficacy of EDO-S101, a First-in-Class Alkylating Histone Deacetylase Inhibition (HDACi) Fusion Molecule, in Relapsed/Refractory Hematologic Malignancies. Clinical Trials Identifier: NCT02576496, Oct. 14, 2015. 5 pages.
ClinicalTrials.gov, Bendamustine, Lenalidomide (Revlimid®) and Dexamethasone (BRd) as 2nd-line Therapy for Patients With Relapsed or Refractory Multiple Myeloma (BRd). Clinical Trials Identifier: NCT01701076, Aug. 24, 2016.
ClinicalTrials.gov, Phase 1 Trial of Dasatinib and Bendamustine in Chronic Lymphocytic Leukemia. ClinicalTrials Identifier: NCT00872976, Apr. 22, 2009. 3 pages.
Clinicaltrials.Gov, Study of EDO-S101, A First-in-Class Alkylating HDACi Fusion Molecule, in Relapsed/Refractory Hematologic Malignancies. ClinicalTrials.gov Identifier: NTC02576496, 4 pages, Oct. 2015.
Clinicaltrials.Gov, Study of the Safety, Pharmacokinetics and Efficacy of EDO-S101, in Patients With Advanced Solid TumorsClinical Trials Identifier: NCT03345485, Dec. 24, 2020. 12 pages.
Connors, Hodgkin lymphoma: special challenges and solutions. Hematol Oncol. Jun. 2015;33 Suppl 1:21-4.
Cooke et al., Spontaneous onset and transplant models of the Vk*MYC mouse show immunological sequelae comparable to human multiple myeloma. J Transl Med. Sep. 6, 2016;14:259. 12 pages.

(56) References Cited

OTHER PUBLICATIONS

Corazzelli et al., Efficacy and safety of bendamustine for the treatment of patients with recurring Hodgkin lymphoma. Br J Haematol. Jan. 2013;160(2):207-15.
Curigliano et al., Cardiovascular toxicity induced by chemotherapy, targeted agents and radiotherapy: ESMO Clinical Practice Guidelines. Annals of Oncology. Oct. 2012;23(Suppl. 7):vii155-vii166.
De Filippi et al., Continuous Exposure to Bendamustine (BDM) Results in Stable Upregulation of CD30 and Increased Sensitivity to Brentuximab Vedotin (BV) in Tumor Cells of Hodgkin Lymphoma HL. Blood. 2015;126(23):2479. 7 pages.
De Filippi et al., Continuous Exposure to Bendamustine (BDM) Results in Stable Upregulation of CD30 and Increased Sensitivity to Brentuximab Vedotin (BV) in Tumor Cells of Hodgkin Lymphoma HL. Istituto Nazionale Tumor, IRCCS-Fondazione Pascale, Dec. 6, 2015. 1 page.
De Filippi et al., Edo-S101, a Bendamustine (BDM)/Histone-Deacetylase Inhibitor (HDACi) Fusion Molecule, Demonstrates Potent Preclinical Activity Against T-Cell Malignancies and Overcomes BDM-Resistance. ASH, 59th Annual Meeting & Exposition. Dec. 9-12, 2017. Poster 2547. 1 page.
De Filippi et al., The First-in-Class Alkylating Histone-Deacetylase Inhibitor (HDACi) Fusion Molecule Edo-S101 Exerts Potent Preclinical Activity Against Tumor Cells of Hodgkin Lymphoma (HL) Including Bendamustine-Resistant Clones. ASH 57th Annual Meeting & Exposition. Abstract No. 2481. Dec. 5-8, 2015 [Downloaded from: [ttps://ash.confex.com/ash/2015/webprogram/Paper84797.html]. 2 pages.
De Filippi et al., The First-in-Class Alkylating Histone-Deacetylase Inhibitor (HDACi) Fusion Molecule Edo-S101 Exerts Potent Preclinical Activity Against Tumor Cells of Hodgkin Lymphoma (HL) Including Bendamustine-Resistant Clones. Blood. 2015;126:2481, 5 pages.
Deangelo et al., Phase 1 clinical results with tandutinib (MLN518), a novel FLT3 antagonist, in patients with acute myelogenous leukemia or high-risk myelodysplastic syndrome: safety, pharmacokinetics, and pharmacodynamics. Blood. Dec. 1, 2006;108(12):3674-81.
Desouza et al., Has the survival of patients with glioblastoma changed over the years? Br J Cancer. Jan. 19, 2016;114(2):146-50.
Detich et al., Valproate induces replication-independent active DNA demethylation. J Biol Chem. Jul. 25, 2003;278(30):27586-92.
Diehl, The Evolution of Chemotherapy, Using the A-DAC Principle to Unlock New Treatment Options in Hodgkin Lymphoma. Mundipharma EDO Satellite Symposium, 10th International Symposium on Hodgkin Lymphoma, 6 pages, Oct. 23, 2016.
Dooley et al., Alkylating Histone Deacetylase Inhibitor Treatment in Animal Models of MPO-ANCA Vasculitis. Abstract TH-PO052. ASN, Kidney Week, Nov. 2, 2017, 2 pages.
Drogaris et al., Histone deacetylase inhibitors globally enhance h3/h4 tail acetylation without affecting h3 lysine 56 acetylation. Sci Rep. 2012;2:220. 12 pages.
Döhner et al., Diagnosis and management of acute myeloid leukemia in adults: recommendations from an international expert panel, on behalf of the European LeukemiaNet. Blood. Jan. 21, 2010;115(3):453-74.
edoncology.com, The A-DAC Principle: A New Concept in Oncology Treatment. 3 pages, Sep. 2016.
EU Clinical Trials Register, EudraCT No. 2005-002051-41. 13 pages. Dec. 7, 2016.
EU Clinical Trials Register, EudraCT No. 2005-006083-57. 28 pages. Jun. 1, 2016.
Eurordis, Rare Diseases Europe, Why Research on Rare Diseases? Position Paper. Retrieved online at: www.eurordis.org. 14 pages. Oct. 2010.
Fei et al., Development of clinically relevant orthotopic xenograft mouse model of metastatic lung cancer and glioblastoma through surgical tumor tissues injection with trocar. J Exp Clin Cancer Res. Jun. 29, 2010;29:84.
Festuccia et al., Enhancement of radiosensitivity by the novel anticancer quinolone derivative vosaroxin in preclinical glioblastoma models. EJC, European Journal of Cancer. Dec. 2016;69(Suppl 1):S62. Abstract 174, Poster P145.
Festuccia et al., Targeting glioblastoma with UniPR1331, a new and stable bioavailable small molecule inhibiting Ephephrin interaction: In vitro and in vivo evidence. EJC, European Journal of Cancer. Dec. 2016;69(Suppl 1), Abstract 71, Poster P042.
Festuccia et al., The first-in-class alkylating deacetylase inhibitor molecule tinostamustine shows antitumor effects and is synergistic with radiotherapy in preclinical models of glioblastoma. J Hematol Oncol. Feb. 27, 2018;11(1):32. 19 pages.
Formenti et al., Results of a phase I-II study of adjuvant concurrent carboplatin and accelerated radiotherapy for triple negative breast cancer. Oncoimmunology. Dec. 27, 2016;6(3):e1274479, 8 pages.
Frew et al., Enhancing the apoptotic and therapeutic effects of HDAC inhibitors. Cancer Lett. Aug. 8, 2009;280(2):125-33.
Furumai et al., Potent histone deacetylase inhibitors built from trichostatin A and cyclic tetrapeptide antibiotics including trapoxin. Proc Natl Acad Sci U S A. Jan. 2, 2001;98(1):87-92.
Gemmill et al., Synergistic growth inhibition by Iressa and Rapamycin is modulated by VHL mutations in renal cell carcinoma. Br J Cancer. Jun. 20, 2005;92(12):2266-77.
Geurink et al., Incorporation of non-natural amino acids improves cell permeability and potency of specific inhibitors of proteasome trypsin-like sites. J Med Chem. Feb. 14, 2013;56(3):1262-75.
Ghesquières et al., Clinical experience of bendamustine in relapsed or refractory Hodgkin lymphoma: a retrospective analysis of the French compassionate use program in 28 patients. Leuk Lymphoma. Nov. 2013;54(11):2399-404.
Gillis, HDAC Inhibition Appears to Sensitive Triple-Negative Breast Cancer Cells to Certain Treatments. Retrieved online at: https://www.onclive.com/conference-coverage/sabcs-2012/hdac-inhibition-appears-to-sensitize-triplenegative-breast-cancer-cells-to-certain-treatment, 2 pages, (2012).
Golub et al., Molecular classification of cancer: class discovery and class prediction by gene expression monitoring. Science. Oct. 15, 1999;286(5439):531-7.
Graham et al., T-cell prolymphocytic leukemia. Proc (Bayl Univ Med Cent). Jan. 2013;26(1):19-21.
Gravina et al., The novel CXCR4 antagonist, PRX177561, reduces tumor cell proliferation and accelerates cancer stem cell differentiation in glioblastoma preclinical models. Tumor Biology. Jun. 2017;1-17.
Greaves et al., Clonal evolution in cancer. Nature. Jan. 18, 2012;481(7381):306-13.
Griffith et al., A novel anti-cancer bifunctional platinum drug candidate with dual DNA binding and histone deacetylase inhibitory activity. Chem Commu (Camb). Nov. 28, 2009;(44):6735-7.
Griffith et al., Novel Platinum Pyridinehydroxamic Acid Complexes: Synthesis, Characterisation, X-ray Crystallographic Study of Nitric Oxide Related Properties. Polyhedron. 2007;26:4697-4706.
Groselj et al., Histone deacetylase inhibitors as radiosensitisers: effects on DNA damage signalling and repair. Br J Cancer. Mar. 5, 2013;108(4):748-54.
Guntner et al., Cerebrospinal fluid penetration of targeted therapeutics in pediatric brain tumor patients. Acta Neuropathol Commun. Jun. 3, 2020;8(1):78, 13 pages.
Hancock et al., HDAC inhibitor therapy in autoimmunity and transplantation. Ann Rheum Dis. Apr. 2012;71 Suppl 2:i46-54.
Harrison et al., High Response Rates with the Combination of Bortezomib. Dexamethasone and the Pan-HistoneDeacetylase Inhibitor Romidepsin in Patients with Relapsed or Refractory Multiple Myeloma in a Phase 1/11 Clinical Trial. Blood. 2008;112, Abstract 3698. ASH Annual Meeting.
Hartmann et al., Bendamustine hydrochloride in patients with refractory soft tissue sarcoma: a noncomparative multicenter phase 2 study of the German sarcoma group (AIO-001). Cancer. Aug. 15, 2007;110(4):861-6.
Hedgethorne et al., FORETINIB, c-Met and VEGFR-2 Inhibitor Oncolytic. Drugs of the Future. 2010;35(11):893-902.
Hegi et al., MGMT gene silencing and benefit from temozolomide in glioblastoma. N Engl J Med. Mar. 10, 2005;352(10):997-1003.

(56) References Cited

OTHER PUBLICATIONS

Her et al., Targeting DNA Double-strand Break Repair in Cancer Therapy. Journal of Molecular and Genetic Medicine. Dec. 31, 2015;9:e106, 1 page.
Herbaux et al., Bendamustine is effective in T-cell prolymphocytic leukaemia. Br J Haematol. Mar. 2015;168(6):916-9.
Herold et al., Bendamustine, vincristine and prednisone (BOP) versus cyclophosphamide, vincristine and prednisone (COP) in advanced indolent non-Hodgkin's lymphoma and mantle cell lymphoma: results of a randomised phase III trial (OSHO# 19). J Cancer Res Clin Oncol. Feb. 2006;132(2):105-12.
Herold et al., BOP versus COP in Advanced Low Grade Non-Hodgkin's Lymphomas—Results of a Randomized Multicenter Study. Blood. 1999;94:262b. Abstract 4382.
Hideshima et al., Mechanism of action of proteasome inhibitors and deacetylase inhibitors and the biological basis of synergy in multiple myeloma. Mol Cancer Ther. Nov. 2011;10(11):2034-42.
Hoffman, Brentuximab Vedotin Plus Bendamustine Active In Heavily Pretreated Hodgkin Lymphoma, ALCL. Cancer Therapy Advisor, Dec. 7, 2015. 2 pages. retreived online at: http://www.cancertherapyadvisor.com/ash-2015/hodgkin-lymphoma-alcl-brentuximab-vedotin-better-treatment-risk/article/458249/.
Hong et al., Complete Durable Response From Carboplatin and Olaparib in a Heavily Pretreated Triple-Negative Metastatic Breast Cancer With Germline BRCA2 and "BRCAness" Mutations. J Oncol Pract. Mar. 2016;12(3):270-2.
Howlader et al., Contributions of Subtypes of Non-Hodgkin Lymphoma to Mortality Trends. Cancer Epidemiol Biomarkers Prev. Jan. 2016;25(1):174-9.
Hummel et al., A pediatric phase 1 trial of vorinostat and temozolomide in relapsed or refractory primary brain or spinal cord tumors: a Children's Oncology Group phase 1 consortium study. Pediatr Blood Cancer. Sep. 2013;60(9):1452-7.
Ihle et al., HR23b expression is a potential predictive biomarker for HDAC inhibitor treatment in mesenchymal tumours and is associated with response to vorinostat. The Journal of Pathology: Clinical Research. 2016;2:59-71.
Jagannath et al., Bortezomib in combination with dexamethasone for the treatment of patients with relapsed and/or refractory multiple myeloma with less than optimal response to bortezomib alone. Haematologica. Jul. 2006;91(7):929-34.
Jawhari et al., In Vitro and In Vivo Preclinical Activity of EDO-S101 in Hodgkin Lymphoma. Haematologica. 2016;101(s5):6-7, Abstract P037.
Jennette et al., Pathogenesis of antineutrophil cytoplasmic autoantibody-mediated disease. Nat Rev Rheumatol. Aug. 2014;10(8):463-73.
Jiang et al., A mammalian functional-genetic approach to characterizing cancer therapeutics. Nature Chemical Biology. Feb. 2011;7:92-100.
Kaddour et al., Transmission of Induced Chromosomal Aberrations through Successive Mitotic Divisions in Human Lymphocytes after In Vitro and ?In? Vivo Radiation. Scientific Reports. Jun. 12, 2017;7:3291, 11 pages.
Kalin et al., Creating zinc monkey wrenches in the treatment of epigenetic disorders. Curr Opin Chem Biol. Jun. 2009;13(3):263-71.
Kallenberg, Pathogenesis and treatment of ANCA-associated vasculitides. Clin Exp Rheumatol. Jul.-Aug. 2015;33(4 Suppl 92):S11-4.
Kallenberg, Pathogenesis of ANCA-associated vasculitides. Ann Rheum Dis. Mar. 2011;70 Suppl 1:i59-63.
Kalsi et al., The impact of low-grade toxicity in older people with cancer undergoing chemotherapy. Br J Cancer. Dec. 9, 2014;111(12):2224-8.
Kampa-Schittenhelm et al., Quizartinib (AC220) is a potent second generation class III tyrosine kinase inhibitor that displays a distinct inhibition profile against mutant-FLT3, -PDGFRA and -KIT isoforms. Molecular Cancer. 2013;12:19, 15 pages.
Kaufman et al., Lenalidomide. Bortezomib. and Dexamethasone (RVD) in Combination with Vorinostat As Front-Line Therapy for Patients with Multiple Myeloma (MM): Results of a Phase 1 Study. Blood. 2012;120, Abstract No. 336. 2 pages. ASH Annual Meeting.
Keating et al., Bendamustine. Nat Rev Drug Discov. Jun. 2008;7(6):473-4.
Khot et al., Panobinostat in lymphoid and myeloid malignancies. Expert Opin Investig Drugs. Sep. 2013;22(9):1211-23.
Kigawa, New strategy for overcoming resistance to chemotherapy of ovarian cancer. Yonago Acta Med. Jun. 2013;56(2):43-50.
Kim et al., Histone deacetylase inhibitors: molecular mechanisms of action and clinical trials as anti-cancer drugs. Am J Transl Res. Feb. 2011;3(2):166-79.
Knauf, Bendamustine in the treatment of chronic lymphocytic leukemia. Expert Rev Anticancer Ther. Feb. 2009;9(2):165-74.
Knittel et al., Two mouse models reveal an actionable PARP1 dependence in aggressive chronic lymphocytic leukemia. Nat Commun. Jul. 28, 2017;8(1):153. 13 pages.
Kollmannsberger et al., Phase II study of bendamustine in patients with relapsed or cisplatin-refractory germ cell cancer. Anticancer Drugs. Aug. 2000;11(7):535-9.
Koster et al., Carboplatin in Combination with Bendamustine in Previously Untreated Patients with Extensive-Stage Small Cell Lung Cancer (SCLC). Clin Drug Investig. 2004;24(10):611-8.
Kotzin et al., Reversal of nzb/nzw disease with total lymphoid irradiation. J Exp Med. Aug 1, 1979;150(2):371-8.
Kraus et al., EDO-S101, A New Alkylating Histone-Deacetylase Inhibitor (HDAC) Fusion Molecule has Superior Activity Against Myeloma and B Cell Lympoma and Strong Synergy, With Proteasome Inhibitors in vitro. ASH, 2014.
Kraus et al., EDO-S101, A New Alkylating Histone-Deacetylase Inhibitor (HDACi) Fusion Molecule, has Superior Activity Against Myeloma and B Cell Lympoma and Strong Synergy With Proteasome Inhibitors in vitro. ASH, 2014. Publication No. 2249.
Kraus et al., EDO-S101, A New Alkylating Histone-Deacetylase Inhibitor (HDACi) Fusion Molecule, Has Superior Activity Against Myeloma and B Cell Lympoma and Strong Synergy with Proteasome Inhibitors in vitro. Blood. 2014;124;2249.
Krause et al., Tyrosine kinases as targets for cancer therapy. N Engl J Med. Jul. 14, 2005;353(2):172-87.
Kumar et al., Histone deacetylase inhibitors induce cell death in supratentorial primitive neuroectodermal tumor cells. Oncol Rep. Nov. 2006;16(5):1047-52.
Lala et al., Role of nitric oxide in tumor progression: lessons from experimental tumors. Cancer Metastasis Rev. Mar. 1998;17(1):91-106.
Layman et al., Severe and prolonged lymphopenia observed in patients treated with bendamustine and erlotinib for metastatic triple negative breast cancer. Cancer Chemother Pharmacol. May 2013;71(5):1183-90.
Le Moigne et al., The p97 Inhibitor CB-5083 Is a Unique Disrupter of Protein Homeostasis in Models of Multiple Myeloma. Molecular Cancer Therapeutics. Nov. 2017;16(11):2375-2386.
Lee et al., Phase I/Ib study of olaparib and carboplatin in BRCA1 or BRCA2 mutation-associated breast or ovarian cancer with biomarker analyses. J Natl Cancer Inst. May 19, 2014;106(6):dju089. 11 pages.
Lehmann et al., Refinement of Triple-Negative Breast Cancer Molecular Subtypes: Implications for Neoadjuvant Chemotherapy Selection. PLoS One. Jun. 16, 2016;11(6):e0157368, 22 pages.
Lentzsch et al., Combination of bendamustine, lenalidomide, and dexamethasone (BLD) in patients with relapsed or refractory multiple myeloma is feasible and highly effective: results of phase 1/2 open-label, dose escalation study. Blood. May 17, 2012;119(20):4608-13.
Leoni et al., Bendamustine (Treanda) displays a distinct pattern of cytotoxicity and unique mechanistic features compared with other alkylating agents. Clin Cancer Res. Jan. 1, 2008;14(1):309-17.
Leoni, Bendamustine: rescue of an effective antineoplastic agent from the mid-twentieth century. Semin Hematol. Apr. 2011;48 Suppl 1:S4-11.
Leung-Hagesteijn et al., Xbp1s-negative tumor B cells and pre-plasmablasts mediate therapeutic proteasome inhibitor resistance in multiple myeloma. Cancer Cell. Sep. 9, 2013;24(3):289-304.

(56) References Cited

OTHER PUBLICATIONS

Li et al., Pharmacokinetics of bendamustine in the central nervous system: chemoinformatic screening followed by validation in a murine model. MedChemComm. 2012;3:1526-1530.

Liby et al., Elevated and Deregulated Expression of HDAC3 in Human Astrocytic Glial Tumours. Folia Biologica (Praha). 2006;52:21-33.

Lin et al., Anti-rheumatic activities of histone deacetylase (HDAC) inhibitors in vivo in collagen-induced arthritis in rodents. Br J Pharmacol. Apr. 2007;150(7):862-72.

Lin et al., Treatment of Brain Metastases. J Clin Oncol. Oct. 20, 2015;33(30):3475-84.

Little et al., Experimental autoimmune vasculitis: an animal model of anti-neutrophil cytoplasmic autoantibody-associated systemic vasculitis. Am J Pathol. Apr. 2009;174(4):1212-20.

Little et al., Therapeutic effect of anti-TNF-alpha antibodies in an experimental model of anti-neutrophil cytoplasm antibody-associated systemic vasculitis. J Am Soc Nephrol. Jan. 2006;17(1):160-9.

Liu et al., A DNA/HDAC dual-targeting drug CY190602 with significantly enhanced anticancer potency. EMBO Mol Med. 12 pages, Published online: Mar. 9, 2015.

Liu et al., Effects of suberoylanilide hydroxamic acid (SAHA) combined with paclitaxel (PTX) on paclitaxel-resistant ovarian cancer cells and insights into the underlying mechanisms. Cancer Cell Int. Nov. 26, 2014;14(1):112, 11 pages.

Liu, Characterization of TCL1-Tg:P53-/-Mice that Resemble Human Chronic Lymphocytic Leukemia with 17P-Deletion. UT GSBS Thesis, Graduate School of Biomedical Sciences, Digital Commons@The Texas Medical Center, May 2013. 142 pages.

Loftsson et al., Historical Perspectives: Cyclodextrins and their pharmaceutical applications. International Journal of Pharmaceutics. 2007;329:1-11.

Loibl et al., Multicenter Phase II Study with Weekly Bendamustine and Paclitaxel as First- or Later-Line Therapy in Patients with Metastatic Breast Cancer: RiTa II Trial. Breast Care (Basel). Dec. 2011;6(6):457-461.

Lombardi et al., Predictors of survival and effect of short (40 Gy) or standard-course (60 Gy) irradiation plus concomitant temozolomide in elderly patients with glioblastoma: a multicenter retrospective study of AINO (Italian Association of Neuro-Oncology). J Neurooncol. Nov. 2015;125(2):359-67.

Lopez-Iglesias et al., Preclinical anti-myeloma activity of EDO-S101, a new bendamustine-derived molecule with added HDACi activity, through potent DNA damage induction and impairment of DNA repair. J Hematol Oncol. Jun. 20, 2017;10(1):127. 14 pages.

Lopez-Iglesias et al., Preclinical anti-myeloma activity of the alkylating-HDACi Fusion Molecule EDO-S101 Through DNA-damaging and HDACi Effects. Haematologica. 2014;99(s1):354-355, Abstract P942.

Lopez-Iglesias et al., Preclinical anti-myeloma activity of the alkylating-HDACi molecule EDO-S101 through DNA-damaging and HDACi effects. EDO, http://mundipharma-edo.com. Poster Jun. 1, 2014.

Lopez-Iglesias et al., Preclinical Anti-Myeloma Activity of the Alkylating-HDACi Molecule EDO-S101 Through DNA-Damaging and HDACi Effects. EHA 2014 Poster, Jun. 12, 2014.

Lopez-Iglesias et al., Preclinical antimyeloma activity of EDO-S101 (bendamustine-vorinostat fusion molecule) through DNA-damaging and HDACi effects. 15th International Myeloma Workshop. Sep. 23-26, 2015. Rome, Italy. Clinical Lymphoma, Myeloma & Leukemia. Sep. 2015;15(3 Suppl. 3):e218, Abstract P0-238.

Lopez-Iglesias et al., The Alkylating Histone Deacetylase Inhibitor Fusion Molecule Edo-S101 Displays Full Bi-Functional Properties in Preclinical Models of Hematological Malignancies. Blood. 2014;124:2100.

Lopez-Iglesias et al., The Hybrid Molecule, Edo-S101, Impairs Double Strand Breaks Repair in Multiple Myeloma and Synergizes with Bortezomib and Dexamethasone. Blood. 2015;126(23):5354-5354.

Lucio-Eterovic et al., Differential expression of 12 histone deacetylase (HDAC) genes in astrocytomas and normal brain tissue: class II and IV are hypoexpressed in glioblastomas. BMC Cancer. Aug. 19, 2008;8:243.

Ludwig et al., Bendamustine-bortezomib-dexamethasone is an active and well-tolerated regimen in patients with relapsed or refractory multiple myeloma. Blood. Feb. 13, 2014;123(7):985-91.

Marchion et al., Development of histone deacetylase inhibitors for cancer treatment. Expert Rev Anticancer Ther. Apr. 2007;7(4):583-98.

Marks, Discovery and development of SAHA as an anticancer agent. Oncogene. Feb. 26, 2007;26(9):1351-6.

Marmion et al., Hydroxamic Acids—An Intriguing Family of Enzyme Inhibitors and Biomedical Ligands. Eur J Inorg Chem. 2004(15):3003-3016.

McInnis et al., Dysregulation of autoantigen genes in ANCA-associated vasculitis involves alternative transcripts and new protein synthesis. J Am Soc Nephrol. Feb. 2015;26(2):390-9.

Meanwell, Synopsis of some recent tactical application of bioisosteres in drug design. J Med Chem. Apr. 28, 2011;54(8):2529-91.

Medline AN—NLM24103869, Chen et al., Dexamethasone and Vorinostat Cooperatively Promote Differentiation and Apoptosis in Kasumi-1 Leukemia Cells Through Ubiquitination and Degradation of AML1-ETO. 2 pages. Sep. 2013.

Medline/NLM AN: NLM24998648, 1 page. May 2014.

Mehrling et al., Activity of the alkylating histone-deacetylase inhibition fusion molecule EDO-S-101 in preclinical models of human glioblastoma independent from MGMT expression. Journal of Clinical Oncology. May 29, 2017;33(Suppl. 15), Abstract e13031.

Mehrling et al., Is there hope to treat glioblastoma effectively? CNS Oncol. 2015;4(6):377-9.

Mehrling et al., The Alkylating-HDAC Inhibition Fusion Principle: Taking Chemotherapy to the Next Level with the First in Class Molecule EDO-S101. Anticancer Agents Med Chem. 2016;16(1):20-8.

Mehrling, Chemotherapy is getting 'smarter'. Future Oncol. 2015;11(4):549-52.

Mehrling, First in human clinical trails to commence Q3 2015. Mundipharma EDO GmbH. Retrieved online at: http://mundipharma-edo.com. Jul. 31, 2015. 2 pages.

Mehrling, First-in-human clinical trial of its lead compound, EDO-S101. Mundipharma EDO GmbH. Retrieved online at: http://mundipharma-edo.com. May 31, 2016. 2 pages.

Mehrling, Fusion Therapy, a New Approach to Combining Treatments. Drug Discovery World. 2016;71-76.

Mehrling, Mundipharma EDO GmbH Announces FDA Investigational New Drug Approval of its First anti-Cancer Compound, EDO-S101, for the Treatment of Patients with Relapsed/Refractory Haematologic Malignancies and Solid Tumours. EDO, http://mundipharma-edo.com/2015/07/31/mundipharma-edo-gmbh-announces-fda-investigational-new-drug-approval-of-its-first-anti-cancer-compound-edo-s101-for-the-treatment-of-patients-with-relapsedrefractory-haematologic-malignancies-and-s/. 2 pages, Jul. 31, 2015.

Mehrling, Mundipharma EDO GmbH announces first-in-human clinical trial of its lead compound, EDO-S101. EDO, http://mundipharma-edo.com/2016/07/20/mundipharma-edo-gmbh-announces-first-in-human-clinical-trial-of-lead-compound-edo-s101/. 2 pages, May 31, 2016.

Mey et al., Bendamustine, lenalidomide and dexamethasone (BRd) has high activity as 2(nd)-line therapy for relapsed and refractory multiple myeloma—a phase II trial. Br J Haematol. Mar. 2017;176(5):770-782.

Miller et al., Histone deacetylase inhibitors. J Med Chem. Nov. 20, 2003;46(24):5097-116.

Min et al., Histone deacetylase inhibitor, suberoylanilide hydroxamic acid (SAHA), enhances anti-tumor effects of the poly (ADP-ribose) polymerase (PARP) inhibitor olaparib in triple-negative breast cancer cells. Breast Cancer Res. Mar. 7, 2015;17:33, 13 pages.

Minucci et al., Histone deacetylase inhibitors and the promise of epigenetic (and more) treatments for cancer. Nat Rev Cancer. Jan. 2006;6(1):38-51.

(56) References Cited

OTHER PUBLICATIONS

Mishra et al., Histone deacetylase inhibitors modulate renal disease in the MRL-lpr/lpr mouse. J Clin Invest. Feb. 2003;111(4):539-52.
Moosman et al., Weekly treatment with a combination of bortezomib and bendamustine in relapsed or refractory indolent non-Hodgkin lymphoma. Leuk Lymphoma. Jan. 2010;51(1):149-52.
Moradei et al., Histone deacetylase inhibitors: latest developments, trends and prospects. Curr Med Chem Anticancer Agents. Sep. 2005;5(5):529-60.
Moreau et al., Phase 1b Dose Escalation Study Of Oral Quisinostat, a Histone Deacetylase Inhibitor (HDACi), In Combination With Velcade (Bortezomib) and Dexamethasone For Patients With Relapsed Multiple Myeloma (MM). Blood. Nov. 15, 2013;122(21):1932.
Moreau et al., Proteasome inhibitors in multiple myeloma: 10 years later. Blood. Aug. 2, 2012;120(5):947-59.
Moscovitch et al., Successful treatment of autoimmune manifestations in MRL/l and MRL/n mice using total lymphoid irradiation (TLI). Exp Mol Pathol. Feb. 1983;38(1):33-47.
Moskowitz et al., Phase II study of bendamustine in relapsed and refractory Hodgkin lymphoma. J Clin Oncol. Feb. 1, 2013;31(4):456-60.
Moskowitz, Bendamustine: a bridge to longer term solutions in heavily treated Hodgkin lymphoma. Leuk Lymphoma. Nov. 2013;54(11):2339-40.
MRF, Melanoma Research Foundation, Melanoma Central Nervous System Metastases, Current Approaches, Challenges and Opportunities. 5 pages (2015).
Munakata et al., The discovery and the development of bendamustine for the treatment of non-Hodgkin lymphoma. Expert Opin Drug Discov. Nov. 2016;11(11):1123-1130.
Munker et al., Activity of Tyrosine Kinase Inhibitors in Multiple Myeloma. Blood. 2007;110(11):274B, Abstract 4804.
National Institute of Health, Cancer. MedlinePlus. Retrieved online at: http://www.nlm.nih.gov/medlineplus/cancer.html. 10 pages. Apr. 16, 2007.
O'Donnell et al., Cancer pharmacoethnicity: ethnic differences in susceptibility to the effects of chemotherapy. Clin Cancer Res. Aug. 1, 2009;15(15):4806-14.
O'Reilly et al., Urinary Soluble CD163 in Active Renal Vasculitis. J Am Soc Nephrol. Sep. 2016;27(9):2906-16.
Ocio et al., Deacetylase Inhibition in Haematological Malignancies—Advanced T-cell Lymphoma, Hodgkin's Lymphoma, Multiple Myeloma, Acute Myelogenous Leukaemia and Myelodysplastic Syndrome. European Haematology. 2010;4:47-50.
Ocio et al., In vitro and in vivo rationale for the triple combination of panobinostat (LBH589) and dexamethasone with either bortezomib or lenalidomide in multiple myeloma. Haematologica. May 2010;95(5):794-803.
Ocio et al., Phase I study of plitidepsin in combination with bortezomib and dexamethasone in patients with relapsed and/or refractory multiple myeloma. Journal of Clinical Oncology. 2016;34:Abstract 8006, 1 page.
Ocio et al., Triple Combinations of the HDAC Inhibitor Panobinostat (LBH589) Plus Dexamethasone with Either Lenalidomide or Bortezomib are Highly Effective in a Multiple Myeloma Mouse Model. Blood. 2007;110:Abstract 1514. ASH Annual Meeting.
Ocio, Epigenetic regulation and HAC inhibitors, Still a role for these agents in MM? Institute of Biomedical Research of Salamanca, University of Salamanca, Cancer Research Center, Slideshow. 32 pages, (2016).
Offidani et al., Efficacy and tolerability of bendamustine, bortezomib and dexamethasone in patients with relapsed-refractory multiple myeloma: a phase II study. Blood Cancer J. Nov. 22, 2013;3:e162.
Ogura et al., A multicentre phase II study of vorinostat in patients with relapsed or refractory indolent B-cell non-Hodgkin lymphoma and mantle cell lymphoma. Br J Haematol. Jun. 2014;165(6):768-76.
Ol et al., Synergistic induction of NY-ESO-1 antigen expression by a novel histone deacetylase inhibitor, valproic acid, with 5-aza-2'-deoxycytidine in glioma cells. J Neurooncol. Mar. 2009;92(1):15-22.
Oken et al., Toxicity and response criteria of the Eastern Cooperative Oncology Group. Am J Clin Oncol. Dec. 1982;5(6):649-55.
Oriol et al., Outcome after relapse of acute lymphoblastic leukemia in adult patients included in four consecutive risk-adapted trials by the PETHEMA Study Group. Haematologica. Apr. 2010;95(4):589-596.
Palmer et al., Combination Cancer Therapy Can Confer Benefit via Patient-to-Patient Variability without Drug Additivity or Synergy. Cell. Dec. 14, 2017;171(7):1678-1691.
Paris et al., Histone deacetylase inhibitors: from bench to clinic. J Med Chem. Mar. 27, 2008;51(6):1505-29.
Phan et al., An update on ethnic differences in drug metabolism and toxicity from anti-cancer drugs. Expert Opin Drug Metab Toxicol. Nov. 2011;7(11):1395-410.
Phiel et al., Histone deacetylase is a direct target of valproic acid, a potent anticonvulsant, mood stabilizer, and teratogen. J Biol Chem. Sep. 28, 2001;276(39):36734-41.
Pitha et al., Parenteral hydroxypropyl cyclodextrins: intravenous and intracerebral administration of lipophiles. J Pharm Sci. Jun. 1994;83(6):833-7.
Poenisch et al., Bendamustine/Prednisone Versus Melphalane/Prednisone in the Primary Treatment of Multiple Myeloma: an Updated Analysis of the 94BP01 Protocol. Blood. 2000;96(Suppl 1:759a), Abstract 3284, Poster Board Session 748-111.
Puetzer et al., Towards novel strategies of targeting specific vulnerabilities of T-PLL cells. AACR Annual Meeting. Jul. 2017;77(Suppl 13), Abstract 1372.
Pönisch et al., Combined bendamustine, prednisone and bortezomib (BPV) in patients with relapsed or refractory multiple myeloma. J Cancer Res Clin Oncol. Mar. 2013;139(3):499-508.
Pönisch et al., Treatment of bendamustine and prednisone in patients with newly diagnosed multiple myeloma results in superior complete response rate, prolonged time to treatment failure and improved quality of life compared to treatment with melphalan and prednisone—a randomized phase III study of the East German Study Group of Hematology and Oncology (OSHO). J Cancer Res Clin Oncol. Apr. 2006;132(4):205-12.
Qian et al., Activity of PXD101, a histone deacetylase inhibitor, in preclinical ovarian cancer studies. Mol Cancer Ther. Aug. 2006;5(8):2086-95.
Rajewski et al., Preliminary safety evaluation of parenterally administered sulfoalkyl ether beta-cyclodextrin derivatives. J Pharm Sci. Aug. 1995;84(8):927-32.
Rang et al., Glucocorticoids. Rang and Dale's Pharmacology, Sixth Edition. Elsevier, Limited, 3 pages, (2007).
Rang et al., Rang and Dale's Pharmacology, Sixth Edition. Churchill Livingstone Elsevier. Chapter 51, p. 729, (2007).
Rasheed et al., Histone deacetylase inhibitors in cancer therapy. Expert Opin Investig Drugs. May 2007;16(5):659-78.
Rasschaert et al., A phase I study of bendamustine hydrochloride administered day 1+2 every 3 weeks in patients with solid tumours. Br J Cancer. Jun. 4, 2007;96(11):1692-8.
Rasschaert et al., A phase I study of bendamustine hydrochloride administered once every 3 weeks in patients with solid tumors. Anticancer Drugs. Jun. 2007;18(5):587-95.
Reagan-Shaw et al., Dose translation from animal to human studies revisited. FASEB J. Mar. 2008;22(3):659-61.
Regna et al., HDAC expression and activity is upregulated in diseased lupus-prone mice. Int Immunopharmacol. Dec. 2015;29(2):494-503.
Reilly et al., Modulation of renal disease in MRL/lpr mice by suberoylanilide hydroxamic acid. J Immunol. Sep. 15, 2004;173(6):4171-8.
Rengstl et al., Small and big Hodgkin-Reed-Sternberg cells of Hodgkin lymphoma cell lines L-428 and L-1236 lack consistent differences in gene expression profiles and are capable to reconstitute each other. PLoS One. May 15, 2017;12(5):e0177378.

(56) References Cited

OTHER PUBLICATIONS

Richardson et al., Panorama 2: panobinostat in combination with bortezomib and dexamethasone in patients with relapsed and bortezomib-refractory myeloma. Blood. Oct. 3, 2013;122(14):2331-7.
Rodriguez-Tenreiro Y Sanchez, Hydrogels of Cyclodextrin Co-crosslinked and Interpenetrated for Controlled Drug Release. University of Santiago de Compostela, School of Pharmacy. pp. 29-32, (2006).
Ryu et al., Valproic acid downregulates the expression of MGMT and sensitizes temozolomide-resistant glioma cells. J Biomed Biotechnol. 2012;2012:987495. 9 pages.
Sampson et al., Vorinostat Enhances Cytotoxicity of SN-38 and Temozolomide in Ewing Sarcoma Cells and Activates STAT3/AKT/MAPK Pathways. PLoS One. Nov. 16, 2015;10(11):e0142704, 19 pages.
Sanchez et al., Anti-Myeloma Effects of Carfilzomib with Cyclophosphamide (CY) or Bendamustine (Ben). Blood. 2012;120(21), Abstract 2952. 54th ASH Annual Meeting adn Exposition.
Santacruz et al., The prognostic impact of minimal residual disease in patients with chronic lymphocytic leukemia requiring first-line therapy. Haematologica. May 2014;99(5):873-80.
Sarkaria et al., Mechanisms of chemoresistance to alkylating agents in malignant glioma. Clin Cancer Res. May 15, 2008;14(10):2900-8.
Saulnier et al., An Efficient Method for the Synthesis of Guanidino Prodrugs. Bioorganic & Medicinal Chemistry Letters. 1994;4(16):1985-1990.
Sawas et al., The Combination of Brentuximab Vedotin (Bv) and Bendamustine (B) Demonstrates Marked Activity in Heavily Treated Patients with Relapsed or Refractory Hodgkin Lymphoma (HL) and Anaplastic Large T-Cell Lymphoma (ALCL): Results of an International Multi Center Phase I/II Experience. Blood. 2015;126:586.
Schöffski et al., Repeated administration of short infusions of bendamustine: a phase I study in patients with advanced progressive solid tumours. J Cancer Res Clin Oncol. Jan. 2000;126(1):41-7.
Schöffski et al., Weekly administration of bendamustine: a phase I study in patients with advanced progressive solid tumours. Ann Oncol. Jun. 2000;11(6):729-34.
Serra et al., Co-clinical trial of olaparib in breast and ovarian patient-derived tumor xenografts (PDX) enables the identification of response biomarkers. Clin Cancer Res. 2016;22(Suppl 16):Abstract B02, 4 pages.
Shah et al., Comprehensive analysis of MGMT promoter methylation: correlation with MGMT expression and clinical response in GBM. PLoS One. Jan. 7, 2011;6(1):e16146.
Shipley et al., Acute myelogenous leukemia. Exp Hematol. Jun. 2009;37(6):649-58.
Siegel et al., Vorinostat in combination with lenalidomide and dexamethasone in patients with relapsed or refractory multiple myeloma. Blood Cancer J. Feb. 21, 2014;4(2):e182, 6 pages.
Simon, Optimal two-stage designs for phase II clinical trials. Control Clin Trials. Mar. 1989;10(1):1-10.
Song et al., Increased expression of histone deacetylase 2 is found in human gastric cancer. APMIS. 2005;113:264-8.
Stiborová et al., The synergistic effects of DNA-targeted chemotherapeutics and histone deacetylase inhibitors as therapeutic strategies for cancer treatment. Curr Med Chem. 2012;19(25):4218-38.
Storer, Design and analysis of phase I clinical trials. Biometrics. Sep. 1989;45(3):925-37.
Sturn et al., Genesis: cluster analysis of microarray data. Bioinformatics. Jan. 2002;18(1):207-8.
Tago et al., Repeated 0.5-Gy gamma irradiation attenuates autoimmune disease in MRL-lpr/lpr mice with suppression of CD3+CD4−CD8−B220+ T-cell proliferation and with up-regulation of CD4+CD25+Foxp3+ regulatory T cells. Radiat Res. Jan. 2008;169(1):59-66.
Takai et al., Human ovarian carcinoma cells: histone deacetylase inhibitors exhibit antiproliferative activity and potently induce apoptosis. Cancer. Dec. 15, 2004;101(12):2760-70.
Tesar et al., Limitations of standard immunosuppressive treatment in ANCA-associated vasculitis and lupus nephritis. Nephron Clin Pract. 2014;128(3-4):205-15.
Thurn et al., Rational therapeutic combinations with histone deacetylase inhibitors for the treatment of cancer. Future Oncol. Feb. 2011;7(2):263-83.
Topalian et al., Immune checkpoint blockade: a common denominator approach to cancer therapy. Cancer Cell. Apr. 13, 2015;27(4):450-61.
Trivedi et al., Management of Chemotherapy-Induced Peripheral Neuropathy. American Journal of Hematology / Oncology. Jan. 2015;11(1):4-10.
Tsai et al., Valproic Acid Enhanced Temozolomide-Induced Anticancer Activity in Human Glioma Through the p53-PUMA Apoptosis Pathway. Front Oncol. Oct. 1, 2021;11:722754, 13 pages.
Tseng et al., A comparison of the molecular subtypes of triple-negative breast cancer among non-Asian and Taiwanese women. Breast Cancer Res Treat. Jun. 2017;163(2):241-254.
Tutt et al., Oral poly(ADP-ribose) polymerase inhibitor olaparib in patients with BRCA1 or BRCA2 mutations and advanced breast cancer: a proof-of-concept trial. Lancet. Jul. 24, 2010;376(9737):235-44.
Valdez et al., Synergistic cytotoxicity of the DNA alkylating agent busulfan, nucleoside analogs and suberoylanilide hydroxamic acid in lymphoma cell lines. Leuk Lymphoma. May 2012;53(5):973-81.
Van Krieken, New developments in the pathology of malignant lymphoma. A review of the literature published from Jan.-Apr. 2016. J Hematop. Jun. 13, 2016;9(2):73-83.
Viel et al., Optimizing glioblastoma temozolomide chemotherapy employing lentiviral-based anti-MGMT shRNA technology. Mol Ther. Mar. 2013;21(3):570-9.
Vippagunta et al., Crystalline Solids. Advanced Drug Delivery Reviews. 2001;48:3-26.
Vlachostergios et al., Bortezomib downregulates MGMT expression in T98G glioblastoma cells. Cell Mol Neurobiol. Apr. 2013;33(3):313-8.
Vlachostergios et al., Bortezomib overcomes MGMT-related resistance of glioblastoma cell lines to temozolomide in a schedule-dependent manner. Invest New Drugs. Oct. 2013;31(5):1169-81.
Von Tresckow et al., An update on emerging drugs for Hodgkin lymphoma. Expert Opin Emerg Drugs. Jun. 2014;19(2):215-24.
Vyas et al., Cyclodextrin based novel drug delivery systems. J Incl Phenom Macrocycl Chem. 2008;62:23-42.
Wang et al., Effect of histone deacetylase inhibitor NL101 on rat neurons. Zhejiang Da Xue Bao Yi Xue Ban. May 2014;43(3):265-272.
Wang et al., Independent validation of a model using cell line chemosensitivity to predict response to therapy. J Natl Cancer Inst. Sep. 4, 2013;105(17):1284-91.
Wang et al., Phase 1 trial of linifanib (ABT-869) in patients with refractory or relapsed acute myeloid leukemia. Leuk Lymphoma. Aug. 2012;53(8):1543-51.
Wang et al., Toward selective histone deacetylase inhibitor design: homology modeling, docking studies, and molecular dynamics simulations of human class I histone deacetylases. J Med Chem. Nov. 3, 2005;48(22):6936-47.
Watanabe et al., Modulation of renal disease in MRL/lpr mice genetically deficient in the alternative complement pathway factor B. J Immunol. Jan. 15, 2000;164(2):786-94.
Weil et al., Breast cancer metastasis to the central nervous system. Am J Pathol. Oct. 2005;167(4):913-20.
White, FDA accepts Mundipharma EDO's IND for EDO-S101. European Pharmaceutical Review. 4 pages, Aug. 3, 2015.
Wiegmans et al., Differences in Expression of Key DNA Damage Repair Genes after Epigenetic-Induced BRCAness Dictate Synthetic Lethality with PARP1 Inhibition. Mol Cancer Ther. Oct. 2015;14(10):2321-31.
Wikipedia, Triple-negative breast cancer. Retrieved online at: https://en.wikipedia.org/wiki/Triple-negative_breast_cancer. 7 pages, Feb. 20, 2017.

(56) References Cited

OTHER PUBLICATIONS

Wilson et al., Histone deacetylase 3 (HDAC3) and other class I HDACs regulate colon cell maturation and p21 expression and are deregulated in human colon cancer. J Biol Chem. May 12, 2006;281(19):13548-58.

Wilson et al., Relationship of p53, bcl-2, and tumor proliferation to clinical drug resistance in non-Hodgkin's lymphomas. Blood. Jan. 15, 1997;89(2):601-9.

Witzel et al., Long-term tumor remission under trastuzumab treatment for HER2 positive metastatic breast cancer—results from the HER-OS patient registry. BMC Cancer. Nov. 4, 2014;14:806. 7 pages.

Xiao et al., Antineutrophil cytoplasmic autoantibodies specific for myeloperoxidase cause glomerulonephritis and vasculitis in mice. J Clin Invest. Oct. 2002;110(7):955-63.

Xie et al., Quantitative structure-activity relationship study of histone deacetylase inhibitors. Curr Med Chem Anticancer Agents. May 2004;4(3):273-99.

Yan et al., Synergistic Inhibition of Tumor Growth and Overcoming Chemo-Resistance by Simultaneously Targeting Key Components in DNA Damage/Repair, Epigenetic, and Putative Cancer Stem Cell Signaling Pathways Using Novel Dual-Functional DNA-Alkylating/HDAC Inhibitor and Tumor Suppressor Gene Nanoparticles in Cancer Research. Cancer Research. Apr. 15, 2012;72(8, Suppl. 1) Proceedings: AACR 103rd Annual Meeting. Abstract 2741. 2 pages.

Yardley, Drug resistance and the role of combination chemotherapy in improving patient outcomes. Int J Breast Cancer. 2013;2013:137414. 15 pages.

Zaja et al., Bendamustine salvage therapy for T cell neoplasms. Ann Hematol. Sep. 2013;92(9):1249-54.

Zhang et al., A novel suberoylanilide hydroxamic acid histone deacetylase inhibitor derivative, N25, exhibiting improved antitumor activity in both human U251 and H460 cells. Asian Pac J Cancer Prev. 2014;15(10):4331-8.

Zhao et al., Comparison of methods for evaluating drug-drug interaction. Front Biosci (Elite Ed). Jan. 1, 2010;2:241-9.

Zhu et al., Histone deacetylase 3 implicated in the pathogenesis of children glioma by promoting glioma cell proliferation and migration. Brain Res. Jul. 3, 2013;1520:15-22.

Zinzani et al., Brentuximab Vedotin in Transplant-Naive Relapsed/Refractory Hodgkin Lymphoma: Experience in 30 Patients. Oncologist. Dec. 2015;20(12):1413-6.

Zinzani et al., Dose Escalation of Tinostamustine in Patients with Relapsed/Refractory (R/R) Lymphoid Malignancies. Retrieved online at: https://library.ehaweb.org/eha/2019/24th/266100/delphine.remmy.dose.escalation.of.tinostamustine.in.patients.with.relapsed.html?f=listing=3*browseby=8*sortby=1*media=1. 1 page, poster presentation. Jun. 1, 2019.

Zulkowski et al., Regression of brain metastases from breast carcinoma after chemotherapy with bendamustine. J Cancer Res Clin Oncol. Feb. 2002;128(2):111-3.

Lin et al., The antiproliferative effect of C2-ceramide on lung cancer cells through apoptosis by inhibiting Akt and NFkB. Cancer Cell Int. Jan. 6, 2014;14(1):1, 7 pages.

U.S. Appl. No. 13/143,155, filed Jul. 1, 2011, U.S. Pat. No. 8,609,864, Granted.
U.S. Appl. No. 14/075,145, filed Nov. 8, 2013, U.S. Pat. No. 9,096,627, Granted.
U.S. Appl. No. 14/972,750, filed Dec. 17, 2015, U.S. Pat. No. Re. 46,144, Granted.
U.S. Appl. No. 14/345,562, filed Nov. 3, 2014, U.S. Pat. No. 9,376,395, Granted.
U.S. Appl. No. 14/374,995, filed Jul. 28, 2014, U.S. Pat. No. 10,118,901, Granted.
U.S. Appl. No. 15/290,546, filed Oct. 11, 2016, 2018/0098969, Abandoned.
U.S. Appl. No. 15/314,162, filed Nov. 28, 2016, 2017/0151218, Abandoned.
U.S. Appl. No. 15/985,097, filed May 21, 2018, U.S. Pat. No. 10,406,138, Granted.
U.S. Appl. No. 16/517,936, filed Jul. 22, 2019, 2019/0343807, Abandoned.
U.S. Appl. No. 17/212,765, filed Mar. 25, 2021, U.S. Pat. No. 11,559,516, Granted.
U.S. Appl. No. 18/086,958, filed Dec. 22, 2022, Pending.
U.S. Appl. No. 15/314,167, filed Nov. 28, 2016, U.S. Pat. No. 9,993,482, Granted.
U.S. Appl. No. 15/314,172, filed Nov. 28, 2016, U.S. Pat. No. 11,419,853, Granted.
U.S. Appl. No. 17/874,621, filed Jul. 27, 2022, 2023/0049350, Published.
U.S. Appl. No. 15/314,180, filed Nov. 28, 2016, U.S. Pat. No. 10,744,120, Granted.
U.S. Appl. No. 16/983,458, filed Aug. 3, 2020, Abandoned.
U.S. Appl. No. 16/994,154, filed Aug. 14, 2020, U.S. Pat. No. 11,541,038, Granted.
U.S. Appl. No. 18/083,651, filed Dec. 19, 2022, Pending.
U.S. Appl. No. 16/341,089, filed Apr. 11, 2019, U.S. Pat. No. 11,266,631, Granted.
U.S. Appl. No. 17/679,308, filed Feb. 24, 2022, 2022/0280485, Allowed.
U.S. Appl. No. 16/621,885, filed Dec. 12, 2019, U.S. Pat. No. 11,576,899, Granted.
U.S. Appl. No. 18/108,736, filed Feb. 13, 2023, Pending.
U.S. Appl. No. 16/621,893, filed Dec. 12, 2019, 2020/0261423, Published.
U.S. Appl. No. 16/621,896, filed Dec. 12, 2019, U.S. Pat. No. 11,413,276, Granted.
U.S. Appl. No. 16/621,898, filed Dec. 12, 2019, U.S. Pat. No. 11,318,117, Granted.
U.S. Appl. No. 17/730,276, filed Apr. 27, 2022, 2022/0401417, Published.
U.S. Appl. No. 17/414,797, filed Jun. 16, 2021, 2022/0016084, Published.
U.S. Appl. No. 17/414,806, filed Jun. 16, 2021, 2022/0016085, Published.

* cited by examiner

Figure 1a

HCC1143 spheroid model, p13

Figure 1b

COMPOUNDS FOR TREATING TNBC

CROSS-REFERENCE TO RELATED APPLICATIONS

This application is a continuation application of U.S. application Ser. No. 16/621,896, filed on Dec. 12, 2019, which is a U.S. national stage filing under 35 U.S.C. § 371(c) of International Application No. PCT/EP2018/065662, filed on Jun. 13, 2018, which claims foreign priority of U.K. Patent Application No. 1709406.1, filed on Jun. 13, 2017. The entire contents of each of the aforementioned applications are incorporated herein by reference.

TECHNICAL FIELD

The present invention relates to methods of treating cancer, particularly triple negative breast cancer (TNBC).

BACKGROUND TO THE INVENTION

Cancer is one of the most life threatening diseases. Cancer is a condition in which cells in a part of the body experience out-of-control growth. According to latest data from American Cancer Society, it is estimated there will be 1.69 million new cases of cancer in USA in 2017. Cancer is the second leading cause of death in the United States (second only to heart disease) and will claim more than 601,000 lives in 2017. In fact, it is estimated the average lifetime risk of developing cancer is 40.8% for American males and 37.5% for American women. Therefore cancer constitutes a major public health burden and represents a significant cost in the United States. These figures are reflected elsewhere across most countries globally, although the types of cancer and relative proportions of the population developing the cancers vary depending upon many different factors such including genetics and diet.

For decades surgery, chemotherapy, and radiation were the established treatments for various cancers. Patients usually receive a combination of these treatments depending upon the type and extent of their disease. But chemotherapy is the most important option for cancer patients when surgical treatment (i.e. the removal of diseased tissue) is impossible. While surgery is sometimes effective in removing tumours located at certain sites, for example, in the breast, colon, and skin, it cannot be used in the treatment of tumours located in other areas, such as the backbone, nor in the treatment of disseminated hematological cancers including cancers of the blood and blood-forming tissues (such as the bone marrow). Such cancers include multiple myeloma, lymphoma and leukemia. Radiation therapy involves the exposure of living tissue to ionizing radiation causing death or damage to the exposed cells. Side effects from radiation therapy may be acute and temporary, while others may be irreversible. Chemotherapy involves the disruption of cell replication or cell metabolism. It is used most often in the treatment of breast, lung, and testicular cancer. One of the main causes of failure in chemotherapy is the development of drug resistance by the cancer cells, a serious problem that may lead to recurrence of disease or even death. Thus, more effective cancer treatments are needed.

Solid tumours are an abnormal mass of tissue that usually does not contain cysts or liquid areas. Solid tumours may be benign (not cancer), or malignant (cancer). Different types of solid tumours are named for the type of cells that form them. Examples of solid tumours are carcinomas and sarcomas. The four most common cancers occurring worldwide are all solid tumours, namely lung, breast, bowel and prostate cancer. These four solid tumour cancers account for around 4 in 10 of all cancers diagnosed worldwide.

According to the National Cancer Institute, there were an estimated 252,170 new cases of and 40,610 deaths due to breast cancer (women only) in the US in 2017.

Breast cancer is the most common noncutaneous cancer in US women, with an estimated 61,000 cases of in situ disease and 246,660 cases of invasive disease in 2016. Thus, fewer than one of six women diagnosed with breast cancer die of the disease. By comparison, it is estimated that about 71,280 American women will die of lung cancer in 2017. Men account for 1% of breast cancer cases and breast cancer death.

Breast cancer is not one form of cancer but consists of many different subtypes of cancers. These subtypes of breast cancer are generally diagnosed based upon the presence (or lack of) three receptors: estrogen receptors, progesterone receptors and human epidermal growth factor receptor 2 (HER2). Around 10-20% of breast cancers test negative for both estrogen and prosegrerone receptors and have HER2 gene amplification, and are known as triple negative breast cancer (TNBC). TNBC tends to be more aggressive than other types of breast cancer and it is more likely to metastasise or recur.

Given the prevalence of solid tumours including breast cancer, there is therefore a need for new effective chemotherapeutic treatments.

In WO-A-2010/085377, the compound of formula I below is disclosed. It is a first-in-class dual-functional alkylating-HDACi fusion molecule which potently inhibits HDAC-regulated pathways.

Biological assays showed that the compound of formula I potently inhibits HDAC enzyme (HDAC1 $IC_{50}$ of 9 nM). The compound of formula I has an INN of tinostamustine and is also known in the art as EDO-S101. It is an AK-DAC (a first-in-class alkylating deacetylase molecule) that, in preclinical studies, has been shown to simultaneously improve access to the DNA strands within cancer cells, break them and block damage repair.

SUMMARY OF THE INVENTION

In a first aspect of the present invention there is provided tinostamustine or a pharmaceutically acceptable salt thereof for use in the treatment of triple negative breast cancer (TNBC) in a patient in need thereof, wherein:
  the TNBC is selected from: basal-like 1 (BL1) subtype; and/or
  the TNBC is BRCA-1 wildtype.

It has surprisingly been discovered that tinostamustine or a pharmaceutically acceptable salt thereof is particularly effective in the treatment of TNBC, with activity data showing strong sensitivity to this compound. Thus, the need for a new and effective treatment of TNBC is met by the present invention.

In a further aspect of the present invention there is provided tinostamustine or a pharmacologically acceptable salt thereof for use as a monotherapy in the treatment of triple negative breast cancer (TNBC) in a patient in need thereof. Optionally:
the TNBC is selected from: basal-like 1 (BL1) subtype; and/or
the TNBC is BRCA-1 wildtype.

In a further aspect of the present invention there is provided the use of tinostamustine or a pharmaceutically acceptable salt thereof for the manufacture of a medicament for the treatment of triple negative breast cancer (TNBC) in a patient in need thereof, wherein:
the TNBC is selected from: basal-like 1 (BL1) subtype; and/or
the TNBC is BRCA-1 wildtype.

In a further aspect of the present invention there is provided the use of tinostamustine or a pharmaceutically acceptable salt thereof as a monotherapy for the manufacture of a medicament for the treatment of triple negative breast cancer (TNBC) in a patient in need thereof. Optionally:
the TNBC is selected from: basal-like 1 (BL1) subtype; and/or
the TNBC is BRCA-1 wildtype.

In a further aspect of the present invention there is provided a method of treating triple negative breast cancer (TNBC) in a patient in need thereof comprising administering to said patient an effective amount of tinostamustine or a pharmaceutically acceptable salt thereof, wherein:
the TNBC is selected from: basal-like 1 (BL1) subtype; and/or
the TNBC is BRCA-1 wildtype.

In a further aspect of the present invention there is provided a method of treating triple negative breast cancer (TNBC) in a patient in need thereof comprising administering to said patient an effective amount of tinostamustine or a pharmaceutically acceptable salt thereof as a monotherapy. Optionally:
the TNBC is selected from: basal-like 1 (BL1) subtype; and/or
the TNBC is BRCA-1 wildtype.

In a further aspect of the present invention there is provided a kit comprising tinostamustine or a pharmaceutically acceptable salt thereof together with instructions for treating triple negative breast cancer (TNBC) in a patient in need thereof, wherein:
the TNBC is selected from: basal-like 1 (BL1) subtype; and/or
the TNBC is BRCA-1 wildtype.

In a further aspect of the present invention there is provided a kit comprising tinostamustine or a pharmaceutically acceptable salt thereof together with instructions for treating triple negative breast cancer (TNBC) as a monotherapy in a patient in need thereof. Optionally:
the TNBC is selected from: basal-like 1 (BL1) subtype; and/or
the TNBC is BRCA-1 wildtype.

In a further aspect, tinostamustine or a pharmaceutically acceptable salt thereof may be administered in combination with one or more further agent(s). The further agent(s) may be DNA repair inhibitors. The further agent(s) may be DNA damage response (DDR) inhibitors. The further agent may be PARP inhibitors. The PARP inhibitor may be olaparib.

The further agent may be carboplatin.

When used in combination, tinostamustine or a pharmaceutically acceptable salt thereof and further agent(s) can be administered concurrently, sequentially or separately. In an embodiment, the agents are administered concurrently. In a further embodiment, the agents are administered sequentially. In a yet further embodiment, the agents are administered separately.

In a further aspect, there is provided a combination comprising tinostamustine or a pharmaceutically acceptable salt thereof and a further agent(s) selected from DNA repair inhibitors, DDR inhibitors, PARP inhibitors, or olaparib.

Combinations of tinostamustine or a pharmaceutically acceptable salt thereof and a further agent(s) selected from DNA repair inhibitors, DDR inhibitors, PARP inhibitors, or olaparib have been found to be particularly effective in the treatment of cancers, such as TNBC, such that they are highly promising in efforts to address the problems of finding more effective treatments of cancer.

Tinostamustine or a pharmaceutically acceptable salt thereof, and further agent(s) can be administered concurrently, sequentially or separately. In an embodiment, the agents are administered concurrently. In a further embodiment, the agents are administered sequentially. In a yet further embodiment, the agents are administered separately.

In a further aspect, there is provided a pharmaceutical composition comprising a pharmaceutically acceptable carrier and a combination according to the present invention.

In a further aspect, there is provided a kit comprising a combination according to the present invention and optionally instructions for treating a patient.

In a further aspect, there is provided a combination according to the present invention for use as a medicament.

In a further aspect, there is provided a combination according to the present invention for use in the treatment of cancer.

In a further aspect, there is provided the use of a combination according to the present invention for the manufacture of a medicament for the treatment of cancer.

In a further aspect, there is provided a method of treating cancer in a patient in need thereof comprising administering a combination according to the present invention.

The following features apply to all aspects of the invention.

The cancer may be TNBC.
The TNBC subtype may be BL1.
The TNBC subtype may be BRCA-1 wildtype.
The TNBC may be relapsed and/or refractory.
The TNBC may be platinum resistant.
The TNBC may be BRCA-1 wildtype.
The cancer may be relapsed and/or refractory.
The cancer may be localized.
The cancer may be metastatic.
The cancer may be advanced.
The cancer may have progressed after at least one line of standard therapy.

One or more further agent(s) may be administered in combination with tinostamustine or a pharmaceutically acceptable salt thereof.

The combination may be tinostamustine or a pharmaceutically acceptable salt thereof and a further agent or agents.
The further agent may be carboplatin.
The further agent(s) may be DNA repair inhibitors.
The further agent(s) may be DDR inhibitors.
The further agent(s) may be PARP inhibitors.

The PARP inhibitor may be olaparib.

The further agents may be carboplatin and a PARP inhibitor.

The DNA repair inhibitors, DDR inhibitors, PARP inhibitors, olaparib may be combined with carboplatin.

The further agents may be carboplatin and olaparib.

DETAILED DESCRIPTION OF THE INVENTION

In the present application, a number of general terms and phrases are used, which should be interpreted as follows.

The compound of formula I has an INN of tinostamustine and is also known in the art as EDO-S101. The IUPAC name is 7-(5-(bis(2-chloroethyl)amino)-1-methyl-1H-benzo[d]imidazol-2-yl)-N-hydroxyheptanamide.

I

"Patient" includes humans, non-human mammals (e.g., dogs, cats, rabbits, cattle, horses, sheep, goats, swine, deer, and the like) and non-mammals (e.g., birds, and the like).

"Pharmaceutically acceptable salts" means salts of compounds of the present invention which are pharmaceutically acceptable, as defined above, and which possess the desired pharmacological activity. Such salts include acid addition salts formed with inorganic acids, or with organic acids. Pharmaceutically acceptable salts also include base addition salts which may be formed when acidic protons present are capable of reacting with inorganic or organic bases. Generally, such salts are, for example, prepared by reacting the free acid or base forms of these compounds with a stoichiometric amount of the appropriate base or acid in water or in an organic solvent or in a mixture of the two. Generally, non-aqueous media like ether, ethyl acetate, ethanol, isopropanol or acetonitrile are preferred. Examples of the acid addition salts include mineral acid addition salts such as, for example, hydrochloride, hydrobromide, hydroiodide, sulfate, bisulfate, sulfamate, nitrate, phosphate, and organic acid addition salts such as, for example, acetate, trifluoroacetate, maleate, fumarate, citrate, oxalate, succinate, tartrate, salicylate, tosylate, lactate, naphthalenesulphonae, malate, mandelate, methanesulfonate and p-toluenesulfonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts.

In the present invention, the pharmaceutically acceptable salt of tinostamustine may preferably be the hydrochloride, hydrobromide, hydroiodide, sulfate, bisulfate, sulfamate, nitrate, phosphate, citrate, methanesulfonate, trifluoroacetate, glutamate, glucuronate, glutarate, malate, maleate, oxalate, succinate, fumarate, tartrate, tosylate, mandelate, salicylate, lactate, p-toluenesulfonate, naphthalenesulfonate or acetate salt.

It has surprisingly been found that tinostamustine or a pharmaceutically acceptable salt thereof shows surprising efficacy in solid tumours. In particular, it has been found that tinostamustine or a pharmaceutically acceptable salt thereof is useful in the treatment of TNBC.

Breast cancer is not one form of cancer but many different subtypes of cancers. These subtypes of breast cancer are generally diagnosed based upon the presence (or lack of) three receptors: estrogen receptors, progesterone receptors and human epidermal growth factor receptor 2 (HER2). Around 10-20% of breast cancers test negative for both estrogen and progesterone receptors and have HER2 gene amplification, and are known as triple negative breast cancer (TNBC).

The absence of these receptors means that the cancers are unlikely to respond to hormonal therapies, including tamoxifen, anastrozole, exemestane, letrozole and fulvestrant). Triple-negative breast cancers are also unlikely to respond to medications that target HER2, such as trastuzumab or lapatinib.

Triple negative breast cancers also tend to be more aggressive than other types of breast cancer and are more likely to metastasise or recur. Five year survival rates also tend to be lower for triple negative breast cancers. For example, a 2007 study of more than 50,000 women with all stages of breast cancer found that 77% of women with triple-negative breast cancer survived at least 5 years, versus 93% of women with other types of breast cancer. Another study of more than 1,600 women published in 2007 found that women with triple-negative breast cancer had a higher risk of death within 5 years of diagnosis, but not after that time period.

Triple negative breast cancer tends to be higher grade than other types of breast cancer, often scoring grade 3 in their appearance and growth patterns.

Triple negative breast cancer represents a heterogeneous diseases and gene expression analysis has identified distinct subtypes, each displaying a unique biology: basal-like (including basal-like 1 (BL1) and basal-like 2 (BL2) subgroups), mesenchymal (M), and luminal androgen receptor (LAR) subtypes (Lehmann et al *Refinement of Triple-Negative Breast Cancer Molecular Subtypes: Implications for Neoadjuvant Chemotherapy Selection*; PLOS 1; 2016 https://doi.org/10.1371/journal.pone.0157368).

The BL1 subtype expresses high levels of genes involved in cell proliferation and DNA damage response. Cell lines linked to the BL1 subtype include HCC1143 (BRCA-1 wild type) and HCC1937 (BRCA-1 negative).

Given the prevalence of TNBC and resistance to current therapies, there is a need for new effective chemotherapeutic treatments.

It has been surprisingly shown that tinostamustine or a pharmaceutically acceptable salt is effective in the treatment of TNBC basal-like 1 (BL1) subgroup. It has further been shown that tinostamustine or a pharmaceutically acceptable salt is effective in the treatment of BRCA-1 wildtype breast cancer.

Tinostamustine or a pharmaceutically acceptable salt has also been shown for the first time to be effective as a monotherapy in the treatment of TNBC.

The therapeutically effective amount of tinostamustine or a pharmaceutically acceptable salt administered to the patient is an amount which confers a therapeutic effect in accordance with the present invention on the treated subject, at a reasonable benefit/risk ratio applicable to any medical treatment. The therapeutic effect may be objective (i.e. measurable by some test or marker) or subjective (i.e. subject gives an indication of or feels an effect). An effective amount of tinostamustine or a pharmaceutically acceptable salt thereof according to the present invention is believed to be one wherein tinostamustine or a pharmaceutically acceptable salt thereof is included at a dosage range of from 0.3 mg/m$^2$ to 300 mg/m$^2$ body surface area of the patient or from 60 mg/m$^2$ to 150 mg/m$^2$ body surface area of the patient. In a preferred embodiment, the dosage range is from 80 mg/m$^2$ to 100 mg/m$^2$ body surface area of the patient.

The specific therapeutically effective dose level for any particular patient will depend upon a variety of factors including the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

"Metastatic Cancer". Cancer has the ability to spread within the body. Cancer cells can spread locally by moving into nearby normal tissue. Cancer can also spread regionally, to nearby lymph nodes, tissues, or organs. Cancer can therefore spread to distant parts of the body. When this happens, it is called metastatic cancer (also known as stage IV cancer), and the process by which cancer cells spread to other parts of the body is called metastasis. Thus, in metastasis, cancer cells break away from where they first formed (primary cancer), travel through the blood or lymph system, and form new tumours (metastatic tumours) in other parts of the body.

Metastatic cancer cells have features like that of the primary cancer and not like the cells in the place where the cancer is found. This enables doctors to tell whether a cancer is metastatic. Metastatic cancers are given the same name as the primary cancer. For example, breast cancer that has spread to the lung is called metastatic breast cancer, not lung cancer. It is treated as stage IV breast cancer, not as lung cancer.

Metastatic TNBC refers to a triple negative breast cancer that has metastasised to a new location in the body. The cancer is treated as a stage IV TNBC.

"Advanced Cancer" is a cancer that is not curable but responds to treatment. Disease directed therapy is still very important because it prolongs life. For terminal cancer, therapy cannot prolong survival significantly due to the progressive nature of the disease and palliative care is the main treatment option.

"Monotherapy" according to the present invention means tinostamustine or a pharmaceutically acceptable salt thereof is administered alone as a single agent. i.e. it is not administered in combination with a further drug or drugs. Examples of such drugs include (but are not limited to) proteasome inhibitors, glucocorticoids and/or tyrosine kinase inhibitors. However, a tinostamustine monotherapy may include radiotherapy.

"DNA repair inhibitors" and "DNA damage response (DDR) inhibitors" target cell repair/response pathways and are a promising therapeutic avenue in cancer therapy. An example is the class of poly(ADP-ribose) polymerase (PARP) inhibitors, including olaparib.

In embodiments of the present invention tinostamustine is administered in combination with a further agent or agents. These agents may include DNA repair inhibitors, DDR inhibitors, PARP inhibitors, olaparib and/or carboplatin. In embodiments, the combinations may exclude proteasome inhibitors, glucocorticoids and/or tyrosine kinase inhibitors.

Suitable examples of the administration form of tinostamustine or a pharmaceutically acceptable salt thereof include without limitation oral, topical, parenteral, sublingual, rectal, vaginal, ocular, and intranasal. Parenteral administration includes subcutaneous injections, intravenous, intramuscular, intrasternal injection or infusion techniques. Preferably, tinostamustine or a pharmaceutically acceptable salt thereof is administered parenterally, and most preferably intravenously.

"BRCA-1 wildtype". BRCA-1 is a gene found on chromosome 17. BRCA-1 is a human gene that produce tumour suppressor proteins. These proteins help repair damaged DNA and, therefore, play a role in ensuring the stability of each cell's genetic material. When either of these genes is mutated, or altered, such that its protein product is not made or does not function correctly, DNA damage may not be repaired properly. As a result, cells are more likely to develop additional genetic alterations that can lead to cancer. Specific inherited mutations in BRCA-1 most notably increase the risk of female breast and ovarian cancers, but they have also been associated with increased risks of several additional types of cancer. People who have inherited mutations in BRCA-1 tend to develop breast and ovarian cancers at younger ages than people who do not have these mutations.

A harmful BRCA-1 mutation can be inherited from a person's mother or father. Each child of a parent who carries a mutation in the gene has a 50% chance (or 1 chance in 2) of inheriting the mutation. The effects of mutations in BRCA-1 are seen even when a person's second copy of the gene is normal.

In contrast, a person who has a BRCA-1 gene which is not mutated has a 'wildtype' i.e. non-mutated gene. BRCA-1 wildtype means a patient who has non-mutated BRCA-1 gene.

A woman's lifetime risk of developing breast cancer is greatly increased if she inherits a harmful mutation in BRCA-1. About 12% of women in the general population will develop breast cancer sometime during their lives. By contrast, a recent large study estimated that about 72% of women who inherit a harmful BRCA-1 mutation will develop breast cancer by the age of 80. Like women from the general population, those with harmful BRCA-1 mutations also have a high risk of developing a new primary cancer in the opposite (contralateral) breast in the years following a breast cancer diagnosis. It has been estimated that, by 20 years after a first breast cancer diagnosis, about 40% of women who inherit a harmful BRCA-1 mutation will develop cancer in their other breast. As such, patients having a mutated BRCA-1 gene carry an increased risk of getting cancer.

At the same time, the presence of mutations on the BRCA-1 gene limits DNA repair pathways of BRCA-1 mutant tumours, making these tumours more susceptible to certain therapies including DNA damaging agents like platinum agents. Thus, patients who are BRCA-1 wildtype may have worse prognosis and outcomes.

Preferably, tinostamustine or a pharmaceutically acceptable salt thereof is administered intravenously to the patient in need thereof at a dosage level to the patient in need thereof of from 0.3 mg/m$^2$ to 300 mg/m$^2$ body surface area of the patient.

Preferably, tinostamustine or a pharmaceutically acceptable salt thereof is administered intravenously to the patient in need thereof at a dosage level to the patient in need thereof of from 60 mg/m$^2$ to 150 mg/m$^2$ body surface area of the patient.

Preferably, tinostamustine or a pharmaceutically acceptable salt thereof is administered intravenously to the patient in need thereof at a dosage level to the patient in need thereof of from 80 mg/m$^2$ to 100 mg/m$^2$ body surface area of the patient.

It has been found that in embodiments of the present invention, tinostamustine or a pharmaceutically acceptable salt thereof or medicament comprising the same may preferably be administered to a patient in need thereof on days 1, 8 and 15 of a 28 day treatment cycle or on days 1 and 15 of a 28 day treatment cycle.

Preferably, tinostamustine or a pharmaceutically acceptable salt thereof is administered on days 1 and 15 of a 28 day treatment cycle.

It has been found that in embodiments of the present invention, tinostamustine or a pharmaceutically acceptable salt thereof or medicament comprising the same may preferably be administered to a patient in need thereof over an infusion time of 60 minutes; or an infusion time of 45 minutes; or an infusion time of 30 minutes.

Preferably, tinostamustine or a pharmaceutically acceptable salt thereof is administered over an infusion time of 60 minutes.

In a preferred embodiment, tinostamustine or a pharmaceutically acceptable salt is administered to the patient in need thereof at a dosage level of from 80 mg/m$^2$ to 100 mg/m$^2$ body surface area of the patient, on days 1 and 15 of a 28 day treatment cycle, over an infusion time of 60 minutes.

In embodiments of the present invention, there is provided a kit comprising tinostamustine or a pharmaceutically acceptable salt thereof or medicament comprising the same together with instructions.

The instructions may advise administering tinostamustine or a pharmaceutically acceptable salt thereof according to variables such as the state of the solid tumours being treated; the age, body weight, general health, sex and diet of the patient; the time of administration, route of administration, and rate of excretion of the specific compounds employed; the duration of the treatment; drugs used in combination or contemporaneously with the specific compounds employed; and like factors well known in the medical arts.

In a further embodiment of the present invention, the patient in need of said treatment is given radiotherapy with (including prior to, during or after) treatment of the solid tumour(s) with tinostamustine or a pharmaceutically acceptable salt thereof. In embodiments of the present invention, the patient is treated with tinostamustine or a pharmaceutically acceptable salt thereof and radiotherapy. Preferably, the patient is given radiotherapy treatment prior to the treatment with tinostamustine or a pharmaceutically acceptable salt thereof. The radiotherapy may be given at a dose of 1 to 5 Gy over 5-10 consecutive days and preferably 2 Gy over 5-10 consecutive days.

In a further embodiment of the present invention, the patient in need of said treatment is given radiotherapy prior to or after treatment of the solid tumours with tinostamustine or a pharmaceutically acceptable salt thereof. Preferably, the patient is given radiotherapy treatment prior to the treatment with tinostamustine or a pharmaceutically acceptable salt thereof. The radiotherapy may be given at a dose of 1 to 5 Gy over 5-10 consecutive days and preferably 2 Gy over 5-10 consecutive days.

When intended for oral administration, tinostamustine or a pharmaceutically acceptable salt thereof or medicament comprising the same may be in solid or liquid form, where semi-solid, semi-liquid, suspension and gel forms are included within the forms considered herein as either solid or liquid.

Tinostamustine or a pharmaceutically acceptable salt thereof or medicament comprising the same can be prepared for administration using methodology well known in the pharmaceutical art. Examples of suitable pharmaceutical formulations and carriers are described in "Remington's Pharmaceutical Sciences" by E. W. Martin.

As a solid composition for oral administration, tinostamustine or a pharmaceutically acceptable salt thereof can be formulated into a powder, granule, compressed tablet, pill, capsule, chewing gum, wafer or the like form. Such a solid composition typically contains one or more inert diluents or carriers. Any inert excipient that is commonly used as a carrier or diluent may be used in compositions of the present invention, such as sugars, polyalcohols, soluble polymers, salts and lipids. Sugars and polyalcohols which may be employed include, without limitation, lactose, sucrose, mannitol, and sorbitol. Illustrative of the soluble polymers which may be employed are polyoxyethylene, poloxamers, polyvinylpyrrolidone, and dextran. Useful salts include, without limitation, sodium chloride, magnesium chloride, and calcium chloride. Lipids which may be employed include, without limitation, fatty acids, glycerol fatty acid esters, glycolipids, and phospholipids.

In addition, one or more of the following can be present: binders such as carboxymethylcellulose, ethyl cellulose, microcrystalline cellulose, or gelatin; excipients such as starch, lactose or dextrins, disintegrating agents such as alginic acid, sodium alginate, corn starch and the like; lubricants such as magnesium stearate; glidants such as colloidal silicon dioxide; sweetening agents such as sucrose or saccharin; a flavoring agent such as peppermint, methyl salicylate or orange flavoring; and a coloring agent.

When tinostamustine or a pharmaceutically acceptable salt thereof compositions is in the form of a capsule (e.g. a gelatin capsule), it can contain, in addition to materials of the above type, a liquid carrier such as polyethylene glycol, cyclodextrin or a fatty oil.

Tinostamustine or a pharmaceutically acceptable salt thereof compositions can be in the form of a liquid, e.g. an elixir, syrup, solution, emulsion or suspension. The liquid can be useful for oral administration or for delivery by injection. When intended for oral administration, tinostamustine or a pharmaceutically acceptable salt thereof compositions can comprise one or more of a sweetening agent, preservatives, dye/colorant and flavor enhancer. In tinostamustine or a pharmaceutically acceptable salt thereof compositions for administration by injection, one or more of a surfactant, preservative, wetting agent, dispersing agent, suspending agent, buffer, stabilizer and isotonic agent can also be included.

The preferred route of administration is parenteral administration including, but not limited to, intradermal, intramuscular, intraperitoneal, intravenous, subcutaneous, intranasal, epidural, intranasal, intracerebral, intraventricular, intrathecal, intravaginal or transdermal. The preferred mode of administration is left to the discretion of the practitioner, and will depend in part upon the site of the medical condition (such as the site of cancer). In a more preferred embodiment, tinostamustine or a pharmaceutically acceptable salt thereof or medicament comprising the same is administered intravenously.

Liquid forms of tinostamustine or a pharmaceutically acceptable salt thereof or medicament comprising the same, may be solutions, suspensions or other like form, and can also include one or more of the following: sterile diluents such as water for injection, saline solution, preferably physiological saline, Ringer's solution, isotonic sodium chloride, fixed oils such as synthetic mono or digylcerides, polyethylene glycols, glycerin, or other solvents; antibacterial agents such as benzyl alcohol or methyl paraben; and agents for the adjustment of tonicity such as sodium chloride or dextrose. A parenteral combination or composition can be enclosed in an ampoule, a disposable syringe or a multiple-dose vial made of glass, plastic or other material. Physiological saline is a preferred adjuvant.

Tinostamustine or a pharmaceutically acceptable salt thereof or medicament comprising the same can be administered by any convenient route, for example by infusion or bolus injection, by absorption through epithelial or mucocutaneous linings, and preferably by bolus.

Examples of compositions comprising tinostamustine or a pharmaceutically acceptable salt thereof are disclosed in WO2013/040286.

The present invention encompasses combinations of tinostamustine or a pharmaceutically acceptable salt and a DNA repair inhibitor.

The present invention encompasses combinations of tinostamustine or a pharmaceutically acceptable salt and a DNA damage response (DDR) inhibitor.

The present invention encompasses combinations of tinostamustine or a pharmaceutically acceptable salt and a PARP inhibitor.

The PARP inhibitor may be olaparib.

The present invention encompasses combinations of tinostamustine or a pharmaceutically acceptable salt and carboplatin. The carboplatin may be administered further in conjunction with a DNA repair inhibitor, a DDR inhibitor, a PARP inhibitor or olaparib.

In one embodiment of the combination of the present invention, tinostamustine or a pharmaceutically acceptable salt thereof and a further agent(s) are adapted for administration concurrently, sequentially or separately. Preferably, tinostamustine or a pharmaceutically acceptable salt thereof and the further agent(s) are adapted for administration concurrently.

The molar ratio of further agent to tinostamustine or a pharmaceutically acceptable salt thereof in the combination of the present invention is typically from 1:2000 to 2000:1. Preferably, the molar ratio of carboplatin to tinostamustine or a pharmaceutically acceptable salt thereof in said combination is from 1:2000 to 1:100, more preferably the molar ratio of carboplatin to tinostamustine or a pharmaceutically acceptable salt thereof in said combination is from 1:1000 to 1:500, and most preferably it is from 1:900 to 1:500, e.g. 1:900, 1:800, 1:700, 1:600 or 1:500.

The further agent may be a DNA repair inhibitor, a DDR inhibitor, a PARP inhibitor, olaparib or carboplatin.

It has been surprisingly found that combinations comprising tinostamustine or a pharmaceutically acceptable salt thereof and a further agent are synergistic combinations. In other words, the potency of the combinations has been measured with the Calcusyn software (biosoft, Ferguson, Mo., USA), which is based on the Chou Talay method (Chou et al., *Adv. Enzyme Regul.*, 22, 27-55 (1984)), that calculates a combination index (CI) with the following interpretation:

CI 1>1: antagonist effect, CI=1: additive effect and CI<1 synergistic effect.

The present invention may be further understood by consideration of the following non-limiting examples.

EXAMPLES

In the following examples, tinostamustine is referred to as EDO-S101.

EDO-S101 may be prepared as described in Example 6 of WO-A-2010/085377.

Example 1

Activity of EDO-S101 in a Triple Negative Breast Cancer Spheroid Model

Materials and Methods

The activity of EDO-S101 alone and in combination was evaluated in triple negative breast cancer (TNBC) cells lines using a spheroid model.

EDO-S101 and Control Compounds

EDO-S101 was provided by EDO MundiPharma, and synthesised as described in Example 6 of WO-A-2010/085377.

Carboplatin was purchased from Sigma.
Paclitaxel was purchased from Sigma.
Olaparib was purchased from Sigma.

Test System

Spherotech TNBC cell line forming multicellular spheroids were prepared for the cell line shown in Table 1.

TABLE 1

| Cell line | Spheroid formation | Site of origin* | Histology# | Molecular subtype | TNBC subtype | BRCA-1 status |
|---|---|---|---|---|---|---|
| HCC1143 | + | PT | IDC | Basal A | BL1 | wt |

Fresh primary triple negative breast cancer samples were obtained after informed consent of the individual patient was given. Patients were recruited following clinical diagnosis, and prior to chemotherapy commencing.

Heterotypic tumour spheroids were prepared from the individual primary breast cancer tissue. The tumour samples were mechanically and enzymatically digested using an enzyme cocktail (Roche, Penzberg Germany), cell viability determined using the trypan-blue exclusion test, and spheroids seeded at a cell density of 50,000 using a modified liquid overlay method. After 48 h in cell culture under standard conditions, successful spheroid formation was documented photographically before starting treatment.

The spheroids were treated with EDO-S101 (5 µM, 10 µM) alone and in combination with carboplatin and/or the PARP inhibitor olaparib (Table 2) for different periods of time (48, 72 h). Solvent controls and an untreated (medium) control was used under the same culture conditions. Treatment efficacy of all drugs was analysed with a standard ATP assay.

TABLE 2

| Single agent | Concentration | Solvent control | Combination therapy |
|---|---|---|---|
| EDO-S101 | 5 µM | DMSO 0.25% | EDO 5 µM + Carboplatin |
| EDO-S101 | 10 µM | DMSO 0.5% | EDO10 µM + Carboplatin |
| Carboplatin (C) | 40.84 µg/ml | H2O 0.41% | EDO 5 µM + Olaparib |
| Paclitaxel (P) | 1.53 µg/ml | NaCl 0.03% | EDO10 µM + Olaparib |
| Olaparib (Ola) | 6.6 µg/ml | DMSO 0.07% | Carboplatin + Olaparib |
| Medium control (untreated) | — | — | Epi + Cyclo + Paclitax |

The results of the experiments are shown in Tables 3a and 3b below. The results are the mean of six repeats per treatment based on the results of the ATP assay.

TABLE 3a

| | HCC1143, p13 | |
|---|---|---|
| Therapy T48 h | mean cell viability * | SD # |
| EDO S101 5 µM | 85.75 | 13.19 |
| EDO S101 10 µM | 57.43 | 2.28 |
| EDO S101 5 µM + Carboplatin | 93.19 | 19.74 |
| EDO S101 10 µM + Carboplatin | 109.25 | 30.02 |
| EDO S101 5 µM + Olaparib | 53.01 | 4.74 |
| EDO S101 10 µM + Olaparib | 68.52 | 6.38 |
| EDO S101 5 µM + Carbopl. + Ola | 82.18 | 13.93 |
| EDO S101 10 µM + Carbo. + Ola | 64.32 | 3.00 |
| Carboplatin | 118.28 | 16.51 |
| Paclitaxel | 92.95 | 8.18 |
| Olaparib | 87.97 | 9.68 |
| Carboplatin + Olaparib | 92.40 | 8.27 |
| Paclitaxel + Olaparib | 85.29 | 2.44 |
| untreated | 107.92 | 2.82 |

TABLE 3b

| | HCC1143 | |
|---|---|---|
| Therapy T72 h | mean cell viability * | SD # |
| EDO S101 5 µM | 79.99 | 12.71 |
| EDO S101 10 µM | 77.09 | 15.36 |
| EDO S101 5 µM + Carboplatin | 93.22 | 12.43 |
| EDO S101 10 µM + Carboplatin | 82.25 | 17.83 |
| EDO S101 5 µM + Olaparib | 47.51 | 2.29 |
| EDO S101 10 µM + Olaparib | 45.22 | 8.11 |
| EDO S101 5 µM + Carbopl. + Ola | 58.15 | 4.14 |
| EDO S101 10 µM + Carbo. + Ola | 52.03 | 3.22 |
| Carboplatin | 105.88 | 8.38 |
| Paclitaxel | 85.59 | 12.72 |
| Olaparib | 61.88 | 11.65 |
| Carboplatin + Olaparib | 105.45 | 5.34 |
| Paclitaxel + Olaparib | 93.17 | 11.77 |
| untreated | 88.55 | 11.14 |

Figure 1A:
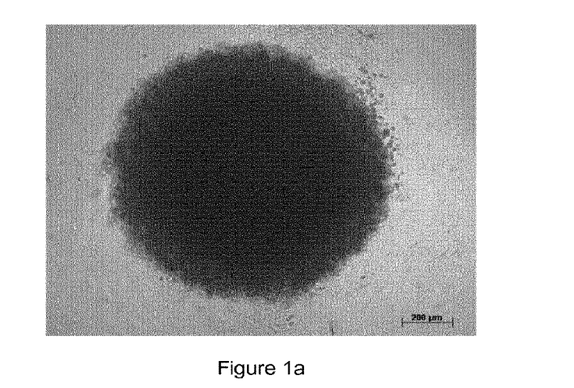
FIG. 1a shows a HCC1143 p13 spheroid after 48 h before starting treatment.
Figure 1B:
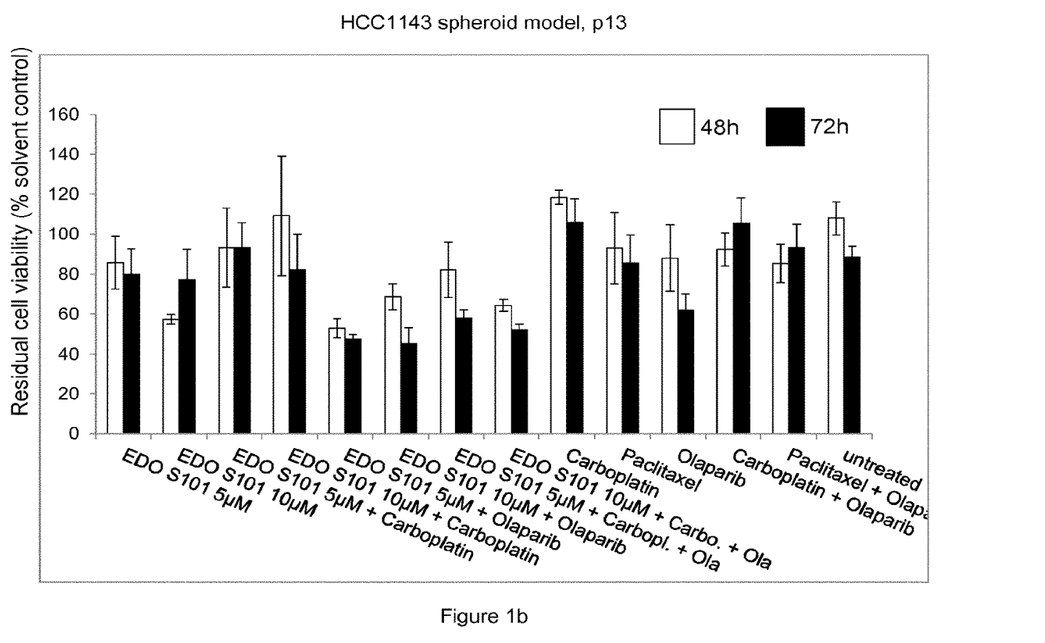
FIG. 1b shows the residual cell viability (% solvent control) of the HCC1143 p13 spheroid model for EDO-S101 alone and in combination with carboplatin and/or olaparib after 48 h and 72 h.

FIG. 1a shows a HCC1143 p13 spheroid 48 h after seeding, and before starting treatment. FIG. 1b shows the residual cell viability (% solvent control) of the HCC1143 p13 spheroid model following treatment with EDO-S101 alone and in combination with carboplatin and/or olaparib after 48 h and 72 h. HCC1143 cells are from the BL1 triple negative breast cancer subtype.

After 48 h, treatment with EDO-S101 (5 µm and 10 µm) alone demonstrated the most enhanced reduction in cell viability (86% and 57% residual cell viability respectively) compared to any of the control agents (carboplatin, paclitaxel, olaparib, or combinations thereof) which range from 85-118%. Treatment with 10 µm EDO-S101 revealed pronounced reduction in cell viability activity against HCC1143 cells. The most pronounced reduction in cell viability (53% residual cell viability) was observed in spheroids treated with EDO-S101 (5 µm)+Ola.

After 72 h treatment with EDO-S101 (5 µM and 10 µM) as a monotherapy, enhanced activity against spheroid cell viability (80% and 77% residual cell viability respectively) compared to the negative control was observed. In addition EDO-S101 monotherapy was more effective than treatment with paclitaxel, carboplatin, C+Ola or P+Ola, but was less effective than Ola alone (62% residual cell viability). However, EDO-S101 (5 µM and 10 µM)+Ola (45% and 48% residual cell viability respectively) demonstrated improved efficacy over Ola as a monotherapy, as did EDO-S101 (5 µM and 10 µM)+Ola+C (58% and 52% residual cell viability respectively). EDO-S101 therefore demonstrated enhanced efficacy against HCC1143 cell viability as compared against Paclitaxel, Carboplatin, Olaparib or any combinations thereof.

FIGS. 1a and 1b demonstrate that EDO-S101 alone has activity against TNBC. The figures also demonstrate that EDO-S101 in combination other cancer drugs also demonstrate activity against TNBC. This is shown in the examples in relation to:

EDO-S101 plus the platinum agent cisplatin;

EDO-S101 plus the PARP inhibitor olaparib;

EDO-S101 plus cisplatin and olaparib.

EDO-S101 is shown to have activity in the BL1 subtype.

EDO-S101 is further shown to have activity in BRCA-1 wild type TNBC, as shown from cell line HCC1143.

Example 3

A Phase 1/2 Study to Investigate the Safety, Pharmacokinetics and Efficacy of EDO-S101, a First-in-Class Alkylating Histone Deacetylase Inhibition (HDACi) Fusion Molecule, in Patients with Advanced Solid Tumors Purpose Phase 1: To determine the safety, tolerability, maximum tolerated dose (MTD), and recommended phase 2 dose (RP2D) of EDO-S101 as a single agent in patients with solid tumors who have progressed after at least one (1) line of standard therapy.

Phase 2: To evaluate the efficacy of EDO-S101 in selected tumor types.

| Condition | Intervention | Phase |
|---|---|---|
| Phase 1:<br>Advanced or metastatic Solid Tumors<br>Phase 2:<br>small cell lung cancer (SCLC)<br>soft tissue sarcoma or non-Kit GIST<br>triple negative breast cancer<br>ovarian cancer | Drug: EDO-S101 | Phase 1/2 |

Study Type: Interventional
Study Design: Intervention Model: Single Group Assignment
  Masking: Open Label
  Primary Purpose: Treatment
  Primary Outcome Measures:
  Phase 1: Dose Escalation until maximum administered dose (MAD):
    Determine Maximum Tolerated Dose at optimal infusion schedule
  Phase 2: Evaluation of Toxicity and Response Rate in Selected Solid Tumor Cohorts:
    Confirm recommended Phase 2 dose and optimal infusion schedule in select solid tumors
    Determine objective response rate and clinical benefit rate in selected solid tumors
  Secondary Outcome Measures:
  Phase 1: Dose Escalation until MAD:
    Determine maximum plasma concentration (Cmax) of EDO-S101
  Phase 2: Evaluation of Toxicity and Response Rate in Selected Solid Tumor Cohorts:
    To evaluate safety and tolerability of the RP2D of the selected schedule of EDOS101.
    To determine the progression free survival time for patients who received the RP2D at the optimal infusion schedule
    To determine overall survival for patients who received the RP2D at the selected study drug administration schedule.
    To establish the trough PK profiles of EDO-S101.
  Estimated Enrollment: 158
  Phase 1:
    Schedule A: EDO-S101, IV, 60 mg/m$^2$ up to 150 mg/m$^2$ Day 1 and 15 of each 28 day cycle
    Schedule B: EDO-S101, IV, 60 mg/m$^2$ up to 150 mg/m$^2$ Day 1, 8 and 15 of each 28 day cycle
    Phase 2:
    The RP2D and selected schedule will be further investigated in patients with specific types of solid tumors: relapsed/refractory SCLC, soft tissue sarcoma, non-Kit GIST, triple negative breast, and ovarian cancers.
Detailed Description:
  EDO-S101 I entity, a first-in-class fusion molecule of an alkylator, bendamustine and a histone-deacetylase inhibitor (HDACi), vorinostat. This phase 1/2 study will enroll patients with solid tumours. This phase 1/2 study will enroll patients with various advanced solid tumours.
  The study consists of 2 phases:
    Phase 1: Dose Escalation until MAD
    Phase 2: Evaluation of Toxicity and Response Rate in Selected Solid Tumor Cohorts
  The study is designed as an open label, Phase 1/2 trial of single agent EDOS101. The phase 1 portion of the study is designed to define the MTD for two (2) administration schedules by evaluating toxicities during dose escalation until MAD. The phase 2 portion of the study is designed to evaluate ORR and CBR at four (4) or six (6) months depending on the type of solid tumor.
  Eligibility
  Ages Eligible for Study: 18 Years and older (Adult, Senior)
  Sexes Eligible for Study: All
  Accepts Healthy Volunteers: No
  Criteria
  Inclusion Criteria for Phase 1 and phase 2 portions of study:
    1. Signed informed consent.
    2. patients ≥18 years at signing the informed consent.
    3. Diagnosis of advanced or metastatic solid tumors, disease should have progressed following at least one line of standard therapy.
    4. Patients with secondary metastasis to the CNS are eligible if they have met certain criteria.
    5. Evaluable disease; either measurable on imaging or with informative tumor marker.
    6. Discontinuation of previous cancer therapies at least three (3) weeks or 5 half-lives, whichever is shorter.
    7. Eastern Cooperative Oncology Group (ECOG) performance status ≤2
    8. Neutrophils ≥1,500 µL.
    9. Platelets ≥100,000 µL.
    10. Aspartate aminotransferase/alanine aminotransferase (AST/ALT)≤3 upper limit of normal (ULN). In cases with liver involvement ALT/AST≤5×ULN.
    11. Total bilirubin ≤1.5 mg/dL unless elevated due to known Gilbert's syndrome.
    12. Creatinine ≤1.5 ULN.
    13. Serum potassium within normal range.
    14. If female of child-bearing potential (i.e. not postmenopausal or surgically sterile), must be willing to abstain from sexual intercourse or employ an effective barrier or medical method of contraception during the study drug administration and follow-up periods. If male, must be sterile or willing to abstain from sexual intercourse or employ a barrier method of contraception during the study treatment and at least 6 months following last treatment.
  Exclusion Criteria for Phase 1 and Phase 2 Portions of Study:
    1. Patients with primary central nervous system (CNS) cancer.
    2. Patients with QTc interval >450 msec for male and >470 msec for female.
    3. Patients who are on treatment with drugs known to prolong the QT/QTc interval.
    4. Patients who are on treatment with Valproic Acid in any of its indication (epilepsy, mood disorder) must be excluded or must stop using the medication.
    5. Any serious medical condition that interferes with adherence to study procedures.
    6. Prior history of solid tumor malignancy diagnosed within the last three (3) years of study enrollment excluding adequately treated basal cell carcinoma of the skin, squamous cell carcinoma of the skin, or in situ cervical cancer, in situ breast cancer, in situ prostate cancer (patients must have shown no evidence of active disease for 2 years prior to enrollment)
    7. Pregnant or breast feeding females.
    8. New York Heart Association (NYHA) stage III/IV congestive heart failure, arrhythmias not adequately controlled, or other significant co-morbidities [e.g. active infection requiring systemic therapy, history of human immunodeficiency virus (HIV) infection, or active Hepatitis B or Hepatitis C].

9. Use of other investigational agents within 30 days or 5 half-lives prior to the first dose of study drug. As long as patient has recovered from any related toxicities ≥Grade 1.

10. Steroid treatment within seven (7) days prior to study treatment. Patients that require intermittent use of bronchodilators, topical steroids or local steroid injections will not be excluded from the study. Patients who have been stabilized to 10 mg orally prednisolone PO QD (or equivalent), daily or less seven (7) days prior to study drug administration are allowed.

Phase 2 Tumor-Specific Eligibility Criteria

Phase 2 patients must meet the cohort-specific inclusion/exclusion criteria in addition to the general inclusion/exclusion criteria for Phase 1 and Phase 2 study listed above.

Cohort 1 Patient Population: Relapsed/Refractory SCLC

1. Histologically or cytological confirmed limited or extensive disease stage of SCLC. The disease should be progressing during or relapsing after the previous treatment.

2. At least one line of prior combination chemotherapy including adequate doses of platinum compound and having progressed during therapy or after the previous treatment.

3. At least 3 weeks or 5 half-lives, whichever is shorter, should have elapsed since prior treatment as long as the patient recovered from any related toxicities to ≤Grade 1.

4. Prior radiotherapy is acceptable provided the patient has recovered from any radiotherapy related acute toxicities.

Cohort 2 Patient Population: Relapsed/Refractory Soft Tissue Sarcoma or Non-Kit GIST 1. Histologically confirmed diagnosis of advanced, unresectable, or metastatic soft tissue sarcoma not amenable to curative treatment with surgery or radiotherapy excluding: chondrosarcoma, neuroblastoma, osteosarcoma, embryonal rhabdomyosarcoma, or Kaposi sarcoma.

2. Must have received at least one prior first line combination chemotherapy regimen or at least two first line single-agent regimens. Adjuvant chemotherapy not considered first line, unless disease progression within 6 months of treatment.

3. The disease should be progressing/relapsed during or after the previous treatment. At least 3 weeks should have elapsed since prior chemotherapy or 5 half-lives, whichever is shorter, as long as the patient recovered from any related toxicities to ≤Grade 1.

4. Presence of measurable disease as defined by the Response Evaluation Criteria in Solid Tumors (RECIST 1.1, Eisenhauer et al. 2009).

Cohort 3 Patient Population: Relapsed/Refractory Triple Negative Breast Cancer

1. Histologically or cytologically confirmed locally advanced or metastatic Triple Negative Metastatic Breast Cancer.

2. Must have received at least one line of chemotherapy, at least 3 weeks should have relapsed since prior chemotherapy or 5 half-lives, whichever is shorter, as long as the patient recovered from acute toxicity of previous therapies to ≤grade 1.

3. Prior radiotherapy is acceptable provided it was applied within 4 four weeks before starting of this trial and the patient recovered from any radiotherapy related acute toxicities.

4. The disease should be progressing/relapsed during or after the previous treatment.

5. Presence of measurable disease as defined by the Response Evaluation Criteria.

Cohort 4 Patient Population: Relapsed/Refractory Ovarian Cancer

1. Histologically or cytologically confirmed advanced ovarian cancer: epithelial ovarian cancer, primary peritoneal cancer or fallopian tube cancer (excluding borderline ovarian cancer) that is resistant or refractory to platinum therapy.

a. Platinum-resistant ovarian cancer is defined as disease that responded to primary platinum therapy and then progressed within 6 months or disease that progressed during or within six months of completing a subsequent platinum therapy.

b. Primary platinum refractory disease is defined as disease that has not responded to a platinum-based regimen or experienced disease recurrence within 3 months of completing a first-line platinum-based regimen.

2. The disease should be progressing/relapsed during or after the previous treatment. At least 3 weeks should have elapsed since prior chemotherapy or 5 half-lives, whichever is shorter, as long as the patient recovered from acute toxicity of previous therapies to ≤grade 1.

3. Presence of measurable disease as defined by the Response Evaluation Criteria in Solid tumors (RECIST 1.1, Eisenhauer et al. 2009).

The invention claimed is:

1. A method of treating triple negative breast cancer (TNBC) in a patient in need thereof, the method comprising administering to the patient a therapeutically effective amount of tinostamustine or a pharmaceutically acceptable salt thereof, wherein: the TNBC is basal-like 1 (BL1) subtype; BRCA-1 wildtype; or a combination thereof.

2. The method of claim 1, wherein tinostamustine or a pharmaceutically acceptable salt thereof is administered in combination with one or more further agent(s).

3. The method according to claim 2, wherein the one or more further agent(s) comprises a PARP inhibitor.

4. The method according to claim 3, wherein the PARP inhibitor is olaparib.

5. The method of claim 2, wherein the one or more further agent(s) comprise a DNA repair inhibitor.

6. The method of claim 2, wherein the one or more further agent(s) comprise a DDR inhibitor.

7. The method of claim 2, wherein tinostamustine and the one or more further agent(s) are administered concurrently, sequentially or separately.

8. The method of claim 1, wherein tinostamustine or a pharmaceutically acceptable salt thereof is administered intravenously to the patient in need thereof at a dosage level of from 0.3 mg/m$^2$ to 300 mg/m$^2$ body surface area of the patient, or from 60 to 150 mg/m$^2$ body surface area of the patient, or from 80 to 100 mg/m$^2$ body surface area of the patient.

9. The method of claim 1, wherein tinostamustine or a pharmaceutically acceptable salt thereof is administered intravenously to the patient in need thereof on days 1, 8 and 15 of a 28 day treatment cycle, or on days 1 and 15 of a 28 day treatment cycle.

10. The method of claim 1, wherein tinostamustine or a pharmaceutically acceptable salt thereof is administered intravenously to the patient in need thereof over an infusion time of 60 minutes; or an infusion time of 45 minutes; or an infusion time of 30 minutes.

11. The method of claim 1, wherein tinostamustine or a pharmaceutically acceptable salt thereof is administered intravenously to the patient in need thereof at a dosage level of from 80 mg/m$^2$ to 100 mg/m$^2$ body surface area of the patient, on days 1 and 15 of a 28 day treatment cycle, and over an infusion time of 60 minutes.

12. The method of claim 1, wherein the patient is treated with tinostamustine or a pharmaceutically acceptable salt thereof and radiotherapy.

13. The method according to claim 12, wherein said radiotherapy treatment is given to the patient in need thereof at a dose of 1 to 5 Gy over 5-10 consecutive days.

14. The method according to claim 12, wherein said radiotherapy treatment is given to the patient in need thereof at a dose of 2 Gy over 5-10 consecutive days.

* * * * *